United States Patent
Lippard et al.

(10) Patent No.: US 7,018,840 B2
(45) Date of Patent: *Mar. 28, 2006

(54) FLUORESCENT METAL SENSORS, AND METHODS OF MAKING AND USING THE SAME

(75) Inventors: Stephen J. Lippard, Cambridge, MA (US); Shawn Burdette, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 323 days.

This patent is subject to a terminal disclaimer.

(21) Appl. No.: 10/124,742

(22) Filed: Apr. 17, 2002

(65) Prior Publication Data

US 2003/0008405 A1 Jan. 9, 2003

Related U.S. Application Data

(60) Provisional application No. 60/284,700, filed on Apr. 17, 2001.

(51) Int. Cl.
*G01N 33/20* (2006.01)

(52) U.S. Cl. .................... 436/73; 564/1; 564/305; 568/18; 568/22; 568/23; 568/25; 568/300; 570/101; 544/1; 546/1; 546/26; 546/79; 546/80; 546/81; 546/82; 546/83; 546/101

(58) Field of Classification Search ............... 436/73; 564/1, 305; 568/18, 22, 23, 25, 300; 570/101; 544/1; 546/1, 26, 79, 80, 81, 82, 83, 101
See application file for complete search history.

(56) References Cited

U.S. PATENT DOCUMENTS

| | | | |
|---|---|---|---|
| 4,510,251 A | 4/1985 | Kirkemo et al. | 436/536 |
| 5,284,934 A | 2/1994 | Allen, Jr. | 530/370 |
| 5,756,771 A | 5/1998 | Mattingly | 549/223 |
| 5,986,094 A | 11/1999 | Ghoshal et al. | 544/230 |
| 6,013,802 A | 1/2000 | Hoyland et al. | 546/18 |
| 6,063,637 A | 5/2000 | Arnold et al. | 436/94 |
| 6,083,758 A | 7/2000 | Imperiali et al. | 436/73 |
| 2003/0068275 A1* | 4/2003 | Lippard et al. | 424/9.36 |

OTHER PUBLICATIONS

Anderegg et al., "Pyridinderivate als Komplexbildner. XI[1]) Die Thermodynamik der Metalkomplexbildung mit Bis-, Tris- und Tetrakis [(2-pyridyl)methyl]-aminen", *Helvetica Chimca Acta*, vol. 60, pp. 123-140 (1977).

Atar et al., "Excitation-Transcription Coupling Mediated by Zinc Influx through Voltage-dependent Calcium channels", *The Journal of Biological Chemistry*, vol. 270, No. 6, Issue of Feb. 10, pp. 2473-2477 (1995).

Belgodere et al., "Imidazolecarboxylic Acids and Their Derivatives. Synthesis of 10H-Imidazo [1, 5-a] Pyrido [1, 2-d] Pyrazin-10-One, A Novel Ring System", *Heterocycles*, vol. 23, No. 2, pp. 349-355 (1985).

(Continued)

*Primary Examiner*—Monique T. Cole
(74) *Attorney, Agent, or Firm*—Dana M. Gordon; Foley Hoag LLP

(57) ABSTRACT

The present invention is directed, in part, to fluorescent metal sensors for detecting metal ions, and methods of making and using the same.

22 Claims, 10 Drawing Sheets

OTHER PUBLICATIONS

Buchen et al., "Copper Complexes of a p-phenylenediamine-based bis(tridentate) ligand", *J. Chem Soc., Dalton Trans.* pp. 2697-2703 (1997).

Budde et al., "Imaging Free Zinc In Synaptic Terminals In Live Hippocampal Slices", *Neuroscience*, vol. 79, No. 2, pp. 347-358 (1997).

Burton et al., "Fluorescein Dyes Derived From 2-Methylresorcinol", *J. Soc. Chem. Inc. London*, vol. 67 pp. 345-347 (1948).

Canzoniero et al., "Measurement of Intracellular Free Zinc in Living Neurons", *Neurobiology of Disease*, vol. 4, pp. 275-279 (1997).

Choi et al, "Zinc and Brain Injury", *Annu. Rev. Neurosci.*, vol. 21, pp. 347-375 (1998).

Copeland et al., "A Chemosensor-Based Approach To Catalyst Discovery in Solution and on Solid Support", *J. Am. Chem. Soc.*, vol. 121, pp. 4306-4307 (1999).

Cuajungco et al., "Zinc Metabolism in the Brain: Relevance to Human Neurodegenerative Disorders", *Neurobiology of Disease*, vol. 4, Article No. NB970163, pp. 137-169 (1997).

Czarnik, A. W., "Desperately Seeking Sensors", *Chemistry & Biology*, vol. 2, No. 7, pp. 423-428 (1995).

da Mota et al., "The Co-ordination Number of Transition-metal Ions. Part VII.[1] An Evaluation of Steric Factors in the Stabilisation of High-spin Five-coordinate Nickel(II) Complexes of Multidendate α-Pyridyl Ligands", *J. Chem. Soc. (A)*, pp. 2036-2042 (1969).

de Silva et al., "Signaling Recognition Events with Fluorescent Sensors and Switches", *Chemical Reviews, American Chemical Society*, vol. 97, pp. 1515-1566 (1997).

Del Zotto et al., "Five-coordinate Diphosphine Complexes of the {CoNO}[8] Group, and their Disproportionation Reactions to Cobalt (III) and {Co(NO)}$_2$[10] Derivatives", *Inorgania Chimica Acta*, vol. 171, pp. 61-69 (1990).

Ebadi et al., "Metallothioneins and Other Zinc-Binding Proteins in Brain", *Methods in Enzymology.*, vol. 205, Part B, pp. 363-387 (1991).

Ebadi et al., "Amino Acid Composition, Immunoreactivity, Sequence Analysis, and Functin of Bovine Hippocampal Metallothionein Isoforms", *Journal of Neurochemistry*, vol. 66, No. 5, pp. 2121-2127 (1996).

Ebadi et al., "Expression And Regulation Of Brain Metallothionein" *Neurochem. Int.*, vol. 27, No. 1, pp. 1-22 (1995).

Evans et al., "Synthesis of γ-Aminobutyryl-γ-aminobutyric Acid", *The Journal of Organic Chemistry*, vol. 24, pp. 863-864 (1959).

Fahrni et al., "Aqueous Coordination Chemistry of Quinoline-Based Fluorescence Probes for the Biological Chemistry of Zinc", *Journal of American Chemical Society*, vol. 121, No. 49, pp. 11448-11458 (1999).

Feig et al., "A Carboxylate-Bridged Non-Heme Diiron Dinitrosyl Complex", *Inorganic Chemistry*, vol. 35, No. 23, pp. 6892-6898 (1996).

Frederickson et al., "Zinc-Containing Neurons", *Biological Signals*, vol. 3, pp. 127-139 (1994).

Frederickson, C., "Neurobiology of Zinc", *International Review of Neurobiology*, vol. 31, pp. 145-238 (1989).

Frederickson et al., "A quinoline fluorescence method for visualizing and assaying the histochemically reactive zinc (bouton zinc) in the brain", *Journal of Neuroscience Methods*, vol. 20, pp. 91-103 (1987).

Gruenwedel, D. W., Multidentate Coordination Compounds. Chelating Properties of Aliphatic Amines Containing *Inorg. Chem.*, vol. 7, pp. 495-501 (1968).

N. L. Harrison et al., "$Zn^{2+}$: an Endogenous Modulator of Ligand- and Voltage-gated Ion channels" *Neuropharmacology*, vol 33, No. 8, pp. 935-952 (1994).

Hartwig et al., "Carbon-Heteroatom Bond-Forming Reductive Eliminations of Amines, Ethers, and Sulfides", *Acc. Chem. Res.*, vol. 31, No. 12, pp. 852-860 (1998).

Hirano et al., "Novel Zinc Fluorescent Probes Excitable with Visible Light for Biological Applications", *Angew. Chem. Int. Ed.*, vol. 39, No. 6, pp. 1052-1054 (2000).

Ulrich Hörlein, "Zur Kenntnis der Tetrahydrocarbolin-Verbin-dungen (I. Mitteil.)", *Chemische Berichte*, vol. 87, No. 4, pp. 463-472 (1954).

Houser et al., "Structural Charaterization of the First Example of a Bis(μ-thiolato)dicopper(II) Complex. Relevance to Proposals for the Electron Transfer Sites in Cyto-chrome c Oxidase and Nitrous Oxide Reductase", *J. Am. Chem. Soc.*, vol. 117, No. 43, pp. 10745-10746 (1995).

Emily P. Huang, "Metal ions And Synaptic Transmission: Think Zinc", *Proc. Natl. Acad. Sci. U.S.A.*, vol. 94, pp 13386-13387 (1997).

Koike et al., "A Novel Biomimetic Zinc(II)-Fluorophore, Dansylamidoethyl-Pendant Macrocyclic Tetraamine 1,4, 710-Tetraazacyclododecane (Cyclen)", *J. Am. Chem. Soc.*, vol. 118, pp. 12696-12703 (1996).

Zoltan Kovacs and A. Dean Sherry, "A General Synthesis of Mono- and Disubstituted 1,4,7-Triazacyclononanes", *Tetrhedron Letters*, vol. 36, No. 51, pp. 9269-9272 (1995).

Mahadevan et al., "The Synthesis of Zinquin Ester and Zinquin Acid, Zinc(II)-Specific Fluorescing Agents for Use in the Study of Biological Zinc(II)" *Aust. J. Chem.* vol. 49, pp. 561-568 (1996).

McBryde, W. A. E., "Spectrophotometric Determination Of Equilibrium Constatns In Solution", *Talanta*, vol. 21, pp. 979-1004 (1974).

Nasir et al., "The chemical cell biology of zinc: structure and intracellular fluorescence of a zinc-quinolinesulfonamide complex" *JBIC*, vol. 4, pp. 775-783 (1999).

Palmiter et al., "Cloning and functional characterization of a mammalian zinc transporter that confers resistance to zinc" *The EMBO Journal*, vol. 14, No. 4, pp. 639-649 (1995).

Palmiter et al., "ZnT-2, a mammalian protein that confers resistance to zinc by facilitating vesicular sequestration", *The EMBO J.*, vol. 15, No. 8, pp. 1784-1791 (1996).

Palmiter et al., "MT-III, a brain-specific member of the metallothionein gene family", *Proc. Natl. Acad. Sci.*, USA, vol. 89, pp. 6333-6337 (1992).

Palmiter et al., "ZnT-3, a putative transporter of zinc into synaptic vesicles", *Proc. Natl. Acad. Sci.*, USA, vol. 93, pp. 14934-14939 (1996).

Pountney et al., "Isolation, primary structures and metal binding properties of neuronal growth inhibitory factor (GIF) from bovine and equine brain" *FEBS Letters*, vol. 345, pp. 193-197 (1994).

Prasad et al., "Synthesis of Gadolinium (±)-100(1-Hydroxypropan-2-yl)-1,4,710-tetraazacyclododecane-1,4,7-triyltriacetate via Tribenzyl 1,4,7,10-Tetraazacyclododecane-1,4,7-tricarboxylate" *J. Chem. Soc. Perkin Trans.*, vol. 1, pp. 3329-3332 (1991).

Romary et al., "New 2~Pyridyl Polyamines. Synthesis, Spectra, and Proton Dissociation Constants", *J. Chem. Soc.*, (C), pp. 2884-2887 (1968).

Sato et al., "Convenient Synthesis of N,N,N'N'-Tetrakis(2-pyridylmethyl)-α, ω-alkanediamines Using a Phase-Transfer Catalyst", *Synthesis*, pp. 539-540 (1992).

Sen et al., "Aldehydofluorescein and Dyes Derived from it", *J. Indian Chem. Soc.*, vol. 6, pp. 505-516 (1929).

Sen et al., "Aldehydo-henolphthalein and Dyes derived from it", *J. Indian Chem. Soc.*, vol. 6, pp. 53-63 (1929).

Shaughnessy et al., "A Fluorescence-Based Assay for High-Throughput Screening of Coupling Reactions. Application to Heck Chemistry", *J. Am. Chem. Soc.*, vol. 121, No. 10, pp. 2123-2132 (1999).

Slomianka, L., "Neurons of Origin of Zinc-containing pathways and the distribution of zinc-containing boutons in the hippocampal region of the rat" *Neuroscience*, vol. 48, No. 2, pp. 325-352 (1992).

Smith et al., "The Design and Properties of a Series of Calcium Indicators which Shift from Rhodamine-like to Fluorescein-like Fluorescence on Binding Calcium", *J. Chem. Sco. Perkin Trans.*, pp. 1195-1204 (1993).

Sun et al., "Synthesis of Fluorinated Fluoresceins", *J. Org. Chem.*, vol. 62, No. 19, pp. 6469-6475 (1997).

Tsien, R.Y., "Fluorescent Probes Of Cell Signaling", *Ann. Rev. Neurosci.*, vol. 12, pp. 227-253 (1989).

Tsuji et al., "Molecular Cloning Of Human Growth Inhibitory Factor cDNA And Its Down-Regulation In Alzheimer's Disease", *EMBO J.*, vol. 11, pp. 4843-4850 (1992).

Uchida et al., "The Growth Inhibitory Factor That Is Deficient In The Alzheimer's Disease Brain Is A 68 Amino Acid Metallothionein-like Protein", *Neuron*, vol. 7, pp. 337-347 (1991).

Vallee et al., "The Biochemical Basis of Zinc Physiology" *Physiological Reviews*, vol. 73, No. 1, pp. 79-118 (1993).

Walkup et al., "A New Cell-Permeable Fluorescent Probe for $Zn^{2+}$", *J. Am. Chem. Soc.*, pp. 5644-5645 (2000).

Wolf, H. U., "Divalent Metal Ion Buffers with Low pH-Sensitivity", *Experientia*, vol. 29, No. 2, pp. 241-249 (1973).

Wolfe et al., "Scope And Limitations Of The Pd/BINAP-Catalyzed Amination Of Aryl Bromides", *J. Org. Chem.*, vol. 65, pp. 1144-1157 (2000).

Wolfe et al., "Simple, Efficient Catalyst System For The Palladium-Catalyzed Amination Of Aryl Chlorides, Bromides, And Triflates", *J. Org. Chem.*, vol. 65, pp. 1158-1174 (2000).

Zalewski et al., "Correlation of apoptosis with change in intracellular labile Zn(II) using Zinquin [(2-methyl-8-p-toluenesulphonamido-6-quinolyloxy) acetic acid], a new specific fluorescent probe for Zn(II)", *Biochem. J.*, vol. 296, pp. 403-4088 (1993).

Zhang et al., "Efficient Synthesis Of N-Aryl-Aza-Crown Ethers via Palladium-Catalyzed Amination", *J. Org. Chem.*, vol. 65, pp. 8027-8031 (2000).

* cited by examiner

FLUORESCENT METAL SENSORS, AND METHODS OF MAKING AND USING THE SAME

RELATED APPLICATION INFORMATION

This application claims the benefit of priority under 35 U.S.C. section 119(e) to Provisional Patent Application No. 60/284,700, filed Apr. 17, 2001. Such provisional patent application is hereby incorporated by reference in its entirety.

GOVERNMENT SUPPORT

The subject invention was made in part with support from the U.S. Government under a grant awarded by the National Cancer Institute, a National Cancer Institute National Research Service Award, and Grant Number 1-R01-GM65519-01 awarded by the NIH. Accordingly, the U.S. Government has certain rights in this invention.

INTRODUCTION

I. Fluorescent Sensors

Fluorescence technology has revolutionized cell biology and many areas of biochemistry. In certain instances, fluorescent molecules may be used to trace molecular and physiological events in living cells. Certain sensitive and quantitative fluorescence detection devices have made fluorescence measurements an ideal readout for in vitro biochemical assays. In addition some fluorescence measurement systems may be useful for determining the presence of analytes in environmental samples. Finally, because certain fluorescence detection systems are rapid and reproducible, fluorescence measurements are often critical for many high-throughput screening applications.

The feasibility of using fluorescence technology for a particular application is often limited by the availability of an appropriate fluorescent sensor. There are a number of features that are desirable in fluorescent sensors, some of which may or may not be present in any particular sensor. First, fluorescent sensors should produce a perceptible change in fluorescence upon binding a desired analyte. Second, fluorescent sensors should selectively bind a particular analyte. Third, to allow concentration changes to be monitored, fluorescent sensors should have a $K_d$ near the median concentration of the species under investigation. Fourth, fluorescent sensors, especially when used intracellularly, should produce a signal with a high quantum yield. Fifth, the wavelengths of both the light used to excite the fluorescent molecule (excitation wavelengths) and of the emitted light (emission wavelengths) are often important. If possible, for intracellular use, a fluorescent sensor should have excitation wavelengths exceeding 340 nm to permit use with glass microscope objectives and prevent UV-induced cell damage, and possess emission wavelengths approaching 500 nm to avoid autofluorescence from native substances in the cell and allow use with typical fluorescence microscopy optical filter sets. Finally, ideal sensors should allow for passive and irreversible loading into cells.

The present invention provides, in part, compounds functionalized at the 6' and optionally the 5' and 7' positions of the fluorescein structure with Lewis bases that bind to metal ions. In part, the present invention is directed to ligands, and methods of making and using the same, that allow for metal ion detection and optionally quantification of its concentration.

II. Zinc in Biological Systems

The importance of metals in biological systems and the general difficulty in measuring metals in living cells makes metal detection a particularly desirable field for the use of fluorescence technology. As, one example, zinc is a vital component in many cellular processes. Although the traditional study of the bioinorganic chemistry of $Zn^{2+}$ has focused on structural and enzymatic functions in proteins, the neurobiology of $Zn^{2+}$ has been gaining attention. Whereas most $Zn^{2+}$ in biological systems is tightly bound in proteins and enzymes, a pool of free $Zn^{2+}$ has been imaged in cells. Sub-nanomolar concentrations of $Zn^{2+}$ has been detected in undifferentiated mammalian cells, and higher concentrations, approaching 300 µM, have been imaged in the mossy fiber terminals of the hippocampus. The $Zn^{2+}$ ion has the ability to modulate a variety of ion channels, may play a role in neuronal death during seizures, is pertinent to neurodegenerative disorders, and may be vital to neurotransmission and long-term potentiation.

Although $Zn^{2+}$ is critical to cellular processes, excess zinc ions can may be toxic. The levels of $Zn^{2+}$ in the brain and other parts of the body are believed to be regulated by three related $Zn^{2+}$ transport proteins (ZnT-1, ZnT-2, and ZnT-3) and by metallothioneins (MTs), including MT-III and MT-IV which are expressed mainly in the brain. ZnTs and MTs are probably responsible for distributing the required $Zn^{2+}$ to proteins and enzymes, and minimizing the amounts of free $Zn^{2+}$ present in cells. In nerve cells, however, free $Zn^{2+}$ is available for neurological functions because $Zn^{2+}$ can be released from synaptic vesicles and can enter cells through voltage-dependent $Ca^{2+}$ channels. Despite the abundance of research, many aspects of ionic $Zn^{2+}$ in neurobiology remain unclear due to the limited detection methods currently available.

In part, the present invention is directed to novel fluorescent sensors for $Zn^{2+}$ and methods for making and using the same.

SUMMARY OF THE INVENTION

In one aspect, the present invention is directed to ligands, and methods of making and using the same. The present invention provides a number of subject compositions that are expected to show changes in their fluorescent properties upon binding to a metal ion. The subject compositions are functionalized at the 6' and optionally 5' and 7' positions of the fluorescein ring structure with a Lewis base that is capable of binding a metal ion. Functionalization of the 4' position with a Lewis base suitable for metal binding is also contemplated. Such functionalization allows for a diverse number of Lewis bases to be used in the subject compositions. Further, certain of the subject compositions are expected to have properties akin to either rhodamine or fluorescein depending on whether they are complexed with a metal ion, which should result in significant changes to the fluorescent properties observed.

The subject compositions, and methods of making and using the same, may achieve a number of desirable results and features, one or more of which (if any) may be present in any particular embodiment of the present invention: (i) fluorescent ligands bind metal ions with a concomitant change in the fluorescence properties of the ligand; (ii) ligands selectively bind a metal ion; (iii) ligands have a $K_d$ near the median concentration of the metal ion under investigation allowing for concentrations of the metal ion to be determined; (iv) ligands exhibit a high quantum yield upon complexation of a metal ion; (v) ligands are capable of in vivo use, and possibly also passive and irreversible loading into cells; and (vi) upon binding a metal of interest, ligands exhibit a shift in emission wavelength, which may be used for visualizing concentration fluctuations and the spatial distribution of dye and analyte.

In one aspect, the present invention is directed to compounds having the following formula:

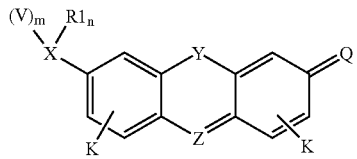

wherein:
X is P or N, preferably N;
Q is O, S or Se or OA as further described below;
K is optionally one or more substituents of the indicated aromatic ring that ideally do not materially detract from the fluorescence of the ligand as described below;
V is independently each a Lewis base capable of forming one or more coordination bonds with a metal ion, and when m is 2, both V appended to X optionally form a ring structure with X;
R1 represents hydrogen, alkyl, cycloalkyl, aryl, aryl, heterocycle, heterocycle or the like, optionally substituted;
m is 1 or 2, and n is equal to (2−m);
Y is O, S, Se, NR1, or $C(CH_3)_3$, wherein R1 and the methyl groups of $C(CH_3)_2$ are optionally substituted; and
Z is N, $HOOCCH_2CH_2C$, HOOC—CH=CH—C, (2-carboxyphenyl)-C, (2-sulfophenyl)-C, (2-carboxy-3,4,5,6-tetrachlorophenyl)-C, (2-carboxy-4-nitrophenyl)-C, (2-carboxy-5-nitrophenyl)-C, (2-carboxy-4-aminophenyl)-C, (2-carboxy-5-aminophenyl)-C, (2,4-dicarboxyphenyl)-C, (2,5-dicarboxylphenyl)-C, (2,4,5-tricarboxyphenyl)C—, and other substituted (2-carboxyphenyl)-C moieties.

For the above formula, if Q is OA, wherein A is hydrogen, alkyl, cycloalkyl, aryl, aryl, heterocycle, heterocycle, a hydroxyl protecting-group or the like, a different tautomer is obtained for the subject ligand, and Z varies accordingly.

In certain preferred embodiments when m is 2, each of V in Formula 1 do not contain—$CO_2H$ as the Lewis base (when deprotonated) to bind the metal ion.

Other subject ligands are depicted in FIG. 2 and below. In still other embodiments, the ligands of the present invention have the structures described in certain of the claims below, all of which claims are hereby incorporated by reference in their entirety into this Summary to describe the present invention.

In another aspect, the subject ligands may be attached to a targeting moiety to direct the ligand to a particular target. For instance, targeting of the subject ligands may allow for detection, and optionally quantification of the concentration of, metal ions at a target cell of interest in vivo.

In another aspect, the present invention is directed to coordination complexes comprising the subject ligands complexed to one or more metal ions.

In another aspect, the present invention provides a number of methods of making the subject compositions.

In another aspect, the subject invention involves methods of using the subject ligands to detect, and optionally to quantify concentrations of, metal ions in a sample. The detection methods rely on the change observed in the fluorescence of the subject ligands upon complexation with a metal ion. Any change observed, both positive and negative, and including, for example, a change in the emission wavelength, the excitation wavelength, and the quantum yield, may be used to detect metal ion complexation. The methods may be used in vivo to detect changes in intracellular concentrations of metal ions with the appropriate ligand. In addition, the present inventive methods provide for positive and negative controls.

In another aspect, the present invention is directed to methods of using the subject ligands for diagnostic purposes. In certain instances, the subject compositions and methods may be used to detect, and optionally to quantify the concentration of, a metal ion of interest of a patient.

In another aspect, the present invention is directed to methods of using the subject ligands for determining the presence of analytes in samples, including samples of environmental interest. In certain aspects, such samples may have a pH of approximately 3, 4 5, 6, 7, 8, 9, 10, 11, 12, or higher.

In other embodiments, this invention contemplates a kit including subject compositions, and optionally instructions for their use. Uses for such kits include, for example, diagnostic applications.

These embodiments of the present invention, other embodiments, and their features and characteristics, will be apparent from the description, drawings and claims that follow.

DETAILED DESCRIPTION OF THE INVENTION

I. Definitions

Figure 1:
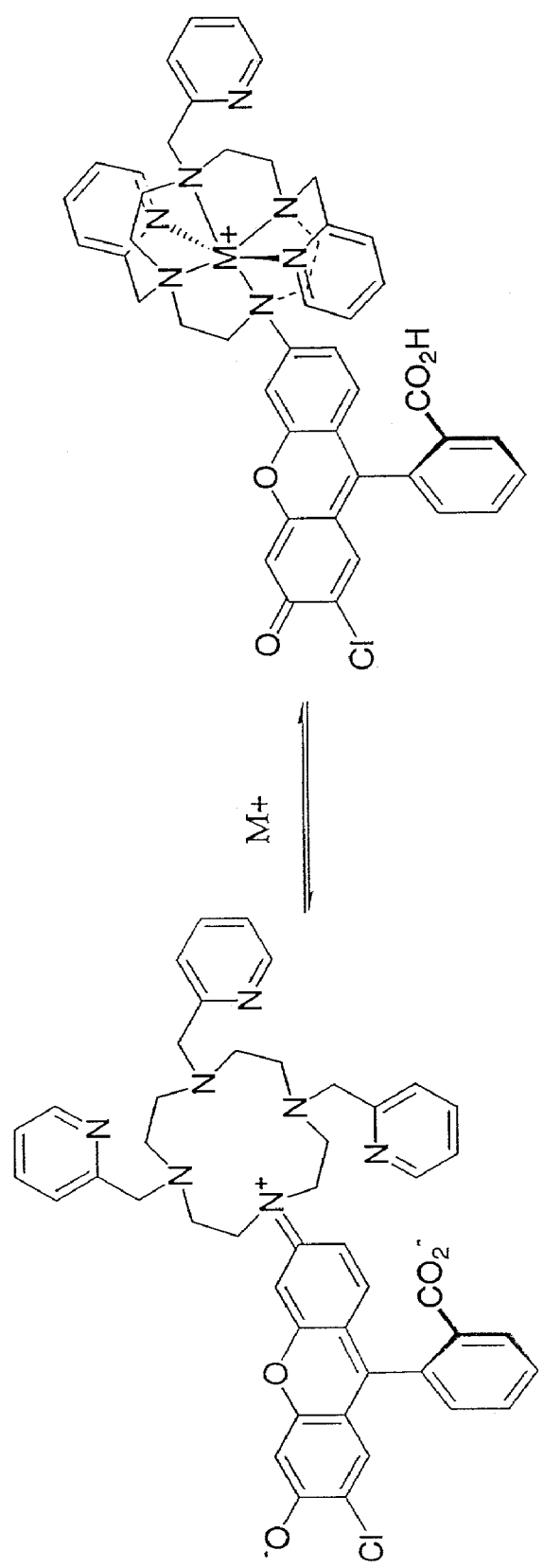
FIG. 1 depicts a subject rhodafluor compound both without a metal ion and coordinated to a metal ion. Although depicted as having a single positive charge, metal ions with charges greater than one are contemplated by this invention.

For convenience, before further description of the present invention, certain terms employed in the specification, examples and appended claims are collected here. These definitions should be read in light of the remainder of the disclosure and understood as by a person of skill in the art.

The articles "a" and "an" are used herein to refer to one or to more than one (i.e., to at least one) of the grammatical object of the article. By way of example, "an element" means one element or more than one element.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below.

The term "ligand" refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "Lewis acid" and "Lewis acidic" are art-recognized and refer to chemical moieties which can accept a pair of electrons from a Lewis base as defined above.

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The terms "coordinate bond" or "coordination bond" refer to an interaction between an electron pair donor and a coordination site on a metal ion leading to an attractive force between the electron pair donor and the metal ion. The use of these terms is not intended to be limiting, in so much as certain coordinate bonds may also be classified as having more or less covalent character (if not entirely covalent character) depending on the nature of the metal ion and the electron pair donor.

The term "coordination site" refers to a point on a metal ion that can accept an electron pair donated, for example, by a liquid or chelating agent.

The term "free coordination site" refers to a coordination site on a metal ion that is vacant or occupied by a species that is weakly donating. Such species is readily displaced by another species, such as a Lewis base.

The term "coordination number" refers to the number of coordination sites on a metal ion that are available for accepting an electron pair.

The term "coordination geometry" refers to the manner in which coordination sites and free coordination sites are spatially arranged around a metal ion. Some examples of coordination geometry include octahedral, square planar, trigonal, trigonal biplanar and others known to those of skill in the art.

The term "complex" means a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A metal ion complex is a coordination complex in which the metal ion is a metal ion. In general, the terms "compound," "composition," "agent" and the like discussed herein include complexes, coordination complexes and metal ion complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a coordination complex is charged, in that the metal ion and any Lewis bases, in the aggregate, are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetraflurorborate, hexafluorophosphate, and monocarboxylates, and dianions such as sulfate. In some cases, coordination complexes themselves may serve as counterions to another coordination complex.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors, including theoretical considerations, such as kinetic versus thermodynamic effects, and the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "synthetic" refers to production by in vitro chemical or enzymatic synthesis.

The term "meso compound" is recognized in the art and means a chemical compound which has at least two chiral centers but is achiral due to a plane or point of symmetry.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product.

An "enantioselective process" is one which favors production of one of the two possible enantiomers of a reaction product.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" refers to molecules with identical chemical constitution and containing more than one stereocenter, but which differ in configuration at only one of these stereocenters.

"Small molecule" is an art-recognized term. In certain embodiments, this term refers to a molecule which has a molecular weight of less than about 2000 amu, or less than about 1000 amu, and even less than about 500 amu.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN, and the like.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged"

rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art recognized and includes an aromatic or non-aromatic ring in which each atom of the ring is carbon. The flowing art-recognized terms have the following meanings: "nitro" means —NO$_2$; the term "halogen" designates —F, —Cl, —Br or —I; the term "sulfhydryl" means —SH; the term "hydroxyl" means —OH; and the term "sulfonyl" means —SO$_2^-$.

The terms "amine" and "amino" are art-recognized and include both unsubstituted and substituted amines, e.g., a moiety that may be represented by the general formulas:

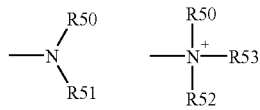

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

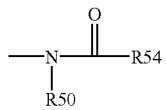

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

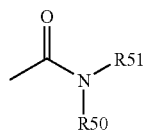

wherein R50 and R51 are as defined above. Certain embodiments of the amide in the present invention will not include imides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

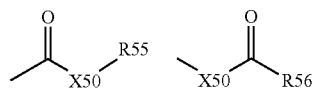

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and includes a moiety that may be represented by the general formula:

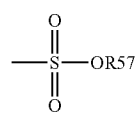

in which R57 is an electron pair, hydrogen, alkyl, cycloalkyl, or aryl.

The term "sulfate" is art recognized and includes a moiety that may be represented by the general formula:

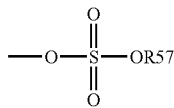

in which R57 is as defined above.

The term "sulfonamido" is art recognized and includes a moiety that may be represented by the general formula:

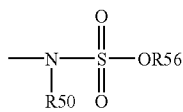

in which R50 and R56 are as defined above.

The term "sulfamoyl" is art-recognized and includes a moiety that may be represented by the general formula:

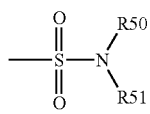

in which R50 and R51 are as defined above.

The term "sulfonyl" is art recognized and includes a moiety that may be represented by the general formula:

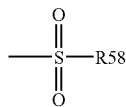

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

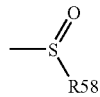

in which R58 is defined above.

The term "phosphoryl" is art recognized and includes moieties represented by the general formula:

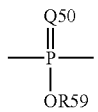

wherein Q50 represents S or O, and R59 represents hydrogen, a lower alkyl or an aryl. When used to substitute, e.g., an alkyl, the phosphoryl group of the phosphorylalkyl may be represented by the general formulas:

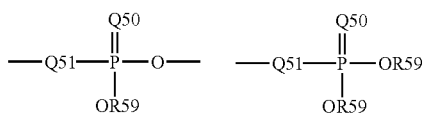

wherein Q50 and R59, each independently, are defined above, and Q51 represents O, S or N. When Q50 is S, the phosphoryl moiety is a "phosphorothioate".

The term "phosphoramidite" is art recognized and includes moieties represented by the general formulas:

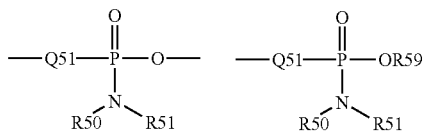

wherein Q51, R50, R51 and R59 are as defined above.

The term "phosphoramidite" is art recognized and includes moieties represented by the general formulas:

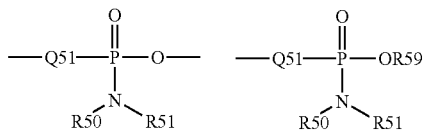

wherein Q51, R50, R51 and R59 are as defined above.

The term "phosphonamidite" is art recognized and includes moieties represented by the general formulas:

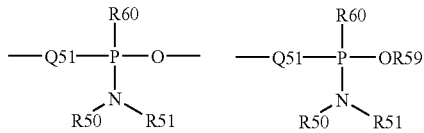

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

The term "selenoalkyl" is art recognized and includes an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compositions of the present invention may exist in particular geometric or stereoisomeric forms. In addition, certain compositions of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. The term "hydrocarbon" is art recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* $2^{nd}$ ed., Wiley, New York, (1991).

The phrase "hydroxyl-protecting group" is art recognized and includes those groups intended to protect a hydroxyl group against undesirable reactions during synthetic procedures and includes, for example, benzyl or other suitable esters or ethers groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251–59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma((P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH($NH_2$)COOH portion, as defined by Kopple, *Peptides and Amino Acids* 2, 33 (W. A. Benjamin Inc., New York and Amsterdam, 1966); examples of such side chains of the common amino acids are —$CH_2CH_2SCH_3$ (the side chain of methionine), —$CH_2CH(CH_3)_2$ (the side chain of leucine) or —H (the side chain of glycine).

The term "amino acid" is intended to embrace all compounds, whether natural or synthetic, which include both an amino functionality and an acid functionality, including amino acid analogs and derivatives. In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compounds may include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers may be obtained in substantially pure form by classical separation techniques and by sterically controlled synthesis. For the purposes of this application, unless expressly noted to the contrary, a named amino acid shall be construed to include both the (D) or (L) stereoisomers. In the majority of cases, D- and L-amino acids have R- and S-absolute configurations, respectively.

The names of the natural amino acids are abbreviated herein in accordance with the recommendations of IUPAC-IUB.

The term "antibody" is intended to include whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

"Human monoclonal antibodies" or "humanized" murine antibodies, as the terms are used herein, refer to murine monoclonal antibodies "humanized" by genetically recombining the nucleotide sequence encoding the murine Fv region (i.e., containing the antigen binding site) or the complementarity-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

"Small molecule" refers to a composition which has a molecular weight of less than about 2000 amu, or less than about 1000 amu, and even less than about 500 amu.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (Candida sp.). Certain target infectious organisms include those that are drug resistant (e.g., Enterobacteriaceae, Enterococcus, *Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

"Target cells", which may serve as the target for the method of the present invention, include prokaryotes and eukaryotes, including yeasts, plant cells and animal cells. The present method may be used to modify cellular function of living cells in vitro, i.e., in cell culture, or in vivo, in which the cells form part of or otherwise exist in plant tissue or animal tissue. Thus the cells may form, for example, the roots, stalks or leaves of growing plants and the present method may be performed on such plant cells in any manner which promotes contact of the targeted construct with the targeted cells. Alternatively, the target cells may form part of the tissue in an animal. Thus the target cells may include, for example, the cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, etc.

The term "targeting moiety" refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

A "patient," "subject" or "host" to be treated by the subject method may mean either a human or non-human animal.

The term "bioavailable" means that a compound the subject invention is in a form that allows for it, or a portion of the amount administered, to be absorbed by, incorporated to, or otherwise physiologically available to a subject or patient to whom it is administered.

The term "pharmaceutically-acceptable salts" refers to the relatively non-toxic, inorganic and organic acid addition salts of compounds, including, for example, coordination complexes of the present invention. The phrases "parenteral administration" and "administered parenterally" are art-recognized terms, and include modes of administration other than enteral and topical administration, such as injections, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is an art-recognized term which includes curing as well as ameliorating at least one symptom of any condition or disease. Diagnostic applications are also examples of "treating".

The phrase "pharmaceutically acceptable" is art-recognized. In certain embodiments, the term includes compositions, ligands and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci., 66:1–19 (1977).

The phrases "systemic administration," "administered systemically," "peripheral administration" and "administered peripherally" are art-recognized, and include the administration of a subject supplement, composition, therapeutic or other material other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient for diagnostic use of the subject compositions. One of ordinary skill in the art may empirically determine the effective amount of a particular compound without necessitating undue experimentation.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

Contemplated equivalents of the subject ligands and other compositions described herein include such materials which otherwise correspond thereto, and which have the same general properties thereof, wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

II. General

A variety of fluorescent ligands, and methods of using and making the same, are contemplated by the present invention. In certain embodiments, the subject ligands form coordination complexes with a variety of metal ions, with a concomitant change in the fluorescent properties of the resulting metal complex as compared to the uncomplexed ligand. In certain embodiment, such ligands may be used to assay for metal ions, including without limitation those that are often referred to as being spectrophotometrically silent, such as $Zn^{2+}$, and the light metals (e.g., $Li^+$, $Mg^{2+}$, $Ca^{2+}$, etc.). A variety of methods of preparing such ligands and the coordination complexes, of assaying for the binding activity of such ligands, and of using such compositions are also taught by the subject invention. A number of different ligands and metal ions are contemplated for the subject coordination complexes, as set out in more detail below.

By way of a general, non-limiting description, fluoresceins exists in three isomeric forms that are favored under different conditions shown below. The free acid is favorable under aqueous conditions and in polar solvents, the lactone is present in non-polar media, and the zwitterion is an isolable intermediate. Addition of acetate, benzoate or silyl protecting groups to the phenols imposes the lactone isomer. In a stable lactone form, fluoresceins may be purified by standard experimental techniques and identified by NMR and IR spectroscopy. In general, it is the free acid form of fluorescein, when deprotonated, that accounts for the compounds strong fluorescence.

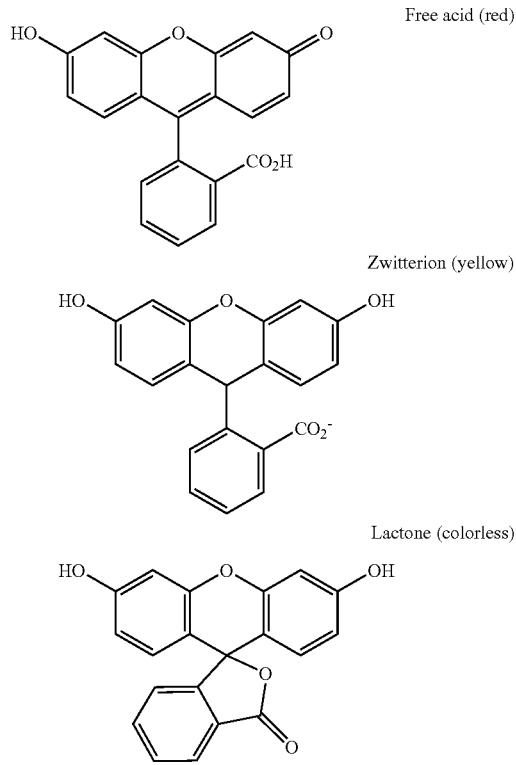

Free acid (red)

Zwitterion (yellow)

Lactone (colorless)

III. Exemplary Fluorescent Ligands.
1. Structures of Subject Compounds

In part, the subject invention is directed to the subject compositions represented by Formula 1:

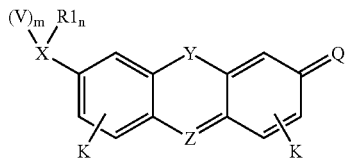

Formula 1 wherein:
X is P or N, preferably N;
Q is O, S, Se or OA as further described below;
K is optionally one or more substituents of the indicated aromatic ring;

V is independently each a Lewis base capable of forming one or more coordination bonds with a metal ion, and when m is 2, both V appended to X optionally form a ring structure with X;

R1 represents hydrogen, alkyl, cycloalkyl, aryl, aryl, heterocycle, heterocycle or the like, optionally substituted;

m is 1 or 2, and n is equal to (2–m);

Y is O, S, Se, NR1, or $C(CH_3)_3$, wherein R1 and the methyl groups of $C(CH_3)_2$ are optionally substituted; and Z is N, $HOOCCH_2CH_2C$, HOOC—CH=CH—C, (2-carboxyphenyl)-C, (2-sulfophenyl)-C, (2-carboxy-3,4,5,6-tetrachlorophenyl)-C, (2-carboxy-4-nitrophenyl)-C, (2-carboxy-5-nitrophenyl)-C, (2-carboxy-4-aminophenyl)-C, (2-carboxy-5-aminophenyl)-C, (2,4-dicarboxyphenyl)-C, (2,5-dicarboxylphenyl)-C, (2,4,5-tricarboxyphenyl)C—, and other substituted (2-carboxyphenyl)-C moieties.

For Formula 1, if Q is OA, wherein A is hydrogen, alkyl, cycloalkyl, aryl, aryl, heterocycle, heterocycle, a hydroxyl protecting-group or the like, a different tautomer is obtained for the subject ligand, and Z varies accordingly.

In certain preferred embodiments, when the preferred metal ion of interest for the subject ligand is a soft metal (such as $Zn^{2+}$), and when m is 2, each of V in Formula 1 do not contain —$CO_2H$ as the Lewis base (when deprotonated) to bind the metal ion.

In certain embodiments, Formula 1 may optionally contain one or more additional Lewis bases for metal ion binding, as depicted below with the optional —A—V substituents:

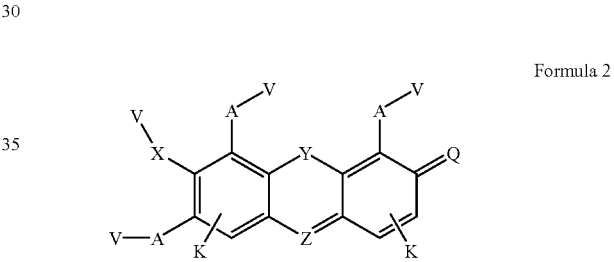

Formula 2 wherein A is one or more carbon atoms, preferably one or two, and the remainder of the moieties are as defined above. Further examples of the subject ligands are set forth in FIG. 2 and otherwise described herein.

Another example of subject compositions is shown in Formula 3:

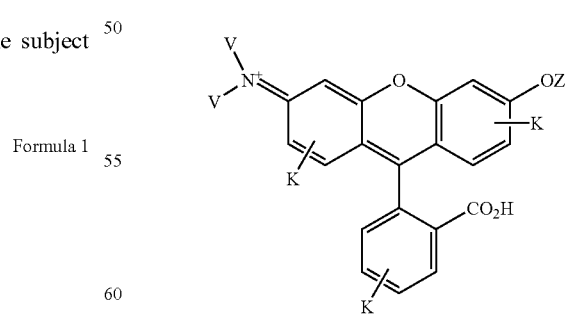

Formula 3

Without wishing to be bound by any theory, or to limit the invention in any way, it is believed that upon in the absence of any metal ion, the subject compositions will exhibit fluorescence properties more akin to rhodamine, whereas upon binding a metal ion, the subject compositions will exhibit fluorescence properties more akin to fluorescein. FIG. 1 depicts the expected behavior for one of the subject compositions. In that example, upon coordination of a metal ion by the aniline nitrogen atom, the nitrogen lone pair becomes decoupled from the fluorophore π-system, and the excitation and emission maxima shift from rhodamine-like to fluorescein-like wavelengths. Because of these properties, the subject compositions may be referred to as "rhodafluor" compounds.

In certain embodiments, A is the alkyl $-CH_2-$ or $-CH_2CH_2-$ or $-CH_2CH_2CH_2-$. In other embodiments, A is $-C(=O)-$, $-C(=S)-$, CHJ, or $CJ_2$, wherein J is a non-interfering substituent in so much as the ligand complexes a metal ion of interest, or $-CH_2-D-$, CHJ—D— or $CJ_2-D-$, etc. where D is any of the foregoing moieties. Examples of J include a halogen, an alkyl group and the like. In certain embodiments, K is —Cl.

In general, K is a chemical moiety that does not preclude using the subject ligands for detection of an analyte of interest. K may be any one or more substituents at any of the aromatic ring carbon positions. In general, the 2' and 7' positions of the fluorescein core is more likely to be substituted, whereas the 1' and 8' positions are less likely to be substituted.

In certain embodiments each K, independently, may be a linear or branched alkyl, alkenyl, linear or branched aminoalkyl, linear or branched acylamino linear or branched acyloxy, linear or branched alkoxycarbonyl, linear or branched alkoxy, linear or branched alkylaryl, linear or branched hydroxyalkyl, linear or branched thioalkyl, acyl, amino, hydroxy, thio, aryloxy, arylalkoxy, hydrogen, alkynyl, halogen, cyano, sulfhydryl, carbamoyl, nitro, trifluoromethyl, amino, thio, lower alkoxy, lower alkylthio, lower alkylamino, nitro, phenoxy, benzyloxy, hydrogen, amine, hydroxyl, alkoxyl, carbonyl, acyl, formyl, sulfonyl and the like.

The identity of K will affect the fluorescence properties of the resulting compound, as known to one of skill in the art. A variety of mechanisms may explain the affect of K on fluorescence, often by quenching, including, for example, double bond torsion, low energy nπ* levels, "heavy" atoms, weak bonds, photoinduced electron transfer (PET) and electronic energy transfer (EET). For example, any K substituents having unpaired electrons at the atom directly attached to the aromatic ring, such as an amine or phenol derivative, are expected to result in quenching of the fluorescence of the uncomplexed ligand. If, however, upon complexation with a metal ion that atom forms a coordinate bond, then quenching through that mechanism should cease, which would give a greater signal for that particular compound upon binding to the analyte of interest.

In preferred embodiments, K is an electron-withdrawing group that is not a Lewis base, such as the halogens and trifluoromethyl, and in particularly preferred embodiments, K is —F or —Cl.

In certain embodiments, V is capable of forming a bidentate chelating agent consisting of an atom of V donating an electron pair and the oxygen atom of the adjacent hydroxyl group(s), if any, of the fluorescein ring structure. Alternatively, V itself includes two or more atoms that serve as Lewis bases and are capable of forming bidentate, tridentate, tretradentate or greater chelating agents by themselves or in conjunction with the oxygen atoms of the hydroxyl substituents of the fluorescein structure (if any). In certain embodiments, the atoms that serve to donate electrons for V are nitrogen, oxygen, sulfur or phosphorus.

In general, V contains a Lewis base fragment that is contemplated to encompass numerous chemical moieties having a variety of structural, chemical and other characteristics capable of forming coordination bonds with a metal ion. The types of functional groups capable of forming coordinate complexes with metal ions are too numerous to categorize here, and are known to those of skill in the art. For example, such moieties will generally include functional groups capable of interaction with a metal center, e.g., heteroatoms such as nitrogen, oxygen, sulfur, and phosphorus.

Metal cations are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties which may be included in V include (assuming appropriate modification of them to allow for their incorporation into V and the subject ligands): amines (primary, secondary, and tertiary) and aromatic amines, amino groups, amido groups, nitro groups, nitroso groups, amino alcohols, nitrites, imino groups, isonitriles, cyanates, isocynates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable V include those chemical moieties containing at least one Lewis basic nitrogen, sulfur, phosphorous or oxygen atom or a combination of such nitrogen, sulfur, phosphorous and oxygen atoms. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents.

Further examples of Lewis base functionality suitable for use in V include the following chemical moieties (assuming appropriate modification of them to allow for their incorporation into V and the subject ligands): amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

Other suitable structural moieties that may be included in V include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates thiocarboxylate and the like.

Other suitable ligand fragments for use in V include structural moieties that are bidentate ligands, including diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable fragments for use in V include ligand fragments that are tridentate ligands, including 2,5 diimino pyridyl ligands, tripyridyl moieties, triimidazoyl moieties, tris pyrazoyl moieties, and combinations of the above ligands.

Other suitable ligand fragments may consist of amino acids or be formed of oligopeptides and the like.

Because the Lewis basic groups function as the coordination site or sites for the metal cation, in certain embodiments, in certain embodiments, it may be preferable that the deformability of the electron shells of the Lewis basic groups and the metal cations be approximately similar. Such a relationship often results in a more stable coordination bond. For instance, sulfur groups may be desirable as the Lewis basic groups when the metal cation is a heavy metal. Some examples include the oligopeptides such as glutathione and cysteine, mercapto ethanol amine, dithiothreitol, amines and peptides containing sulfur and the like. Nitrogen containing groups may be employed as the Lewis basic groups when smaller metal ions are the metal. Alternatively, for those applications in which a less stable coordination bond is desired, it may be desirable that the deformability be dissimilar. These relationships are also characterized by those of skill in the art as "hard" and "soft" metals and Lewis bases.

2. Synthesis of Subject Compounds

Figure 2:
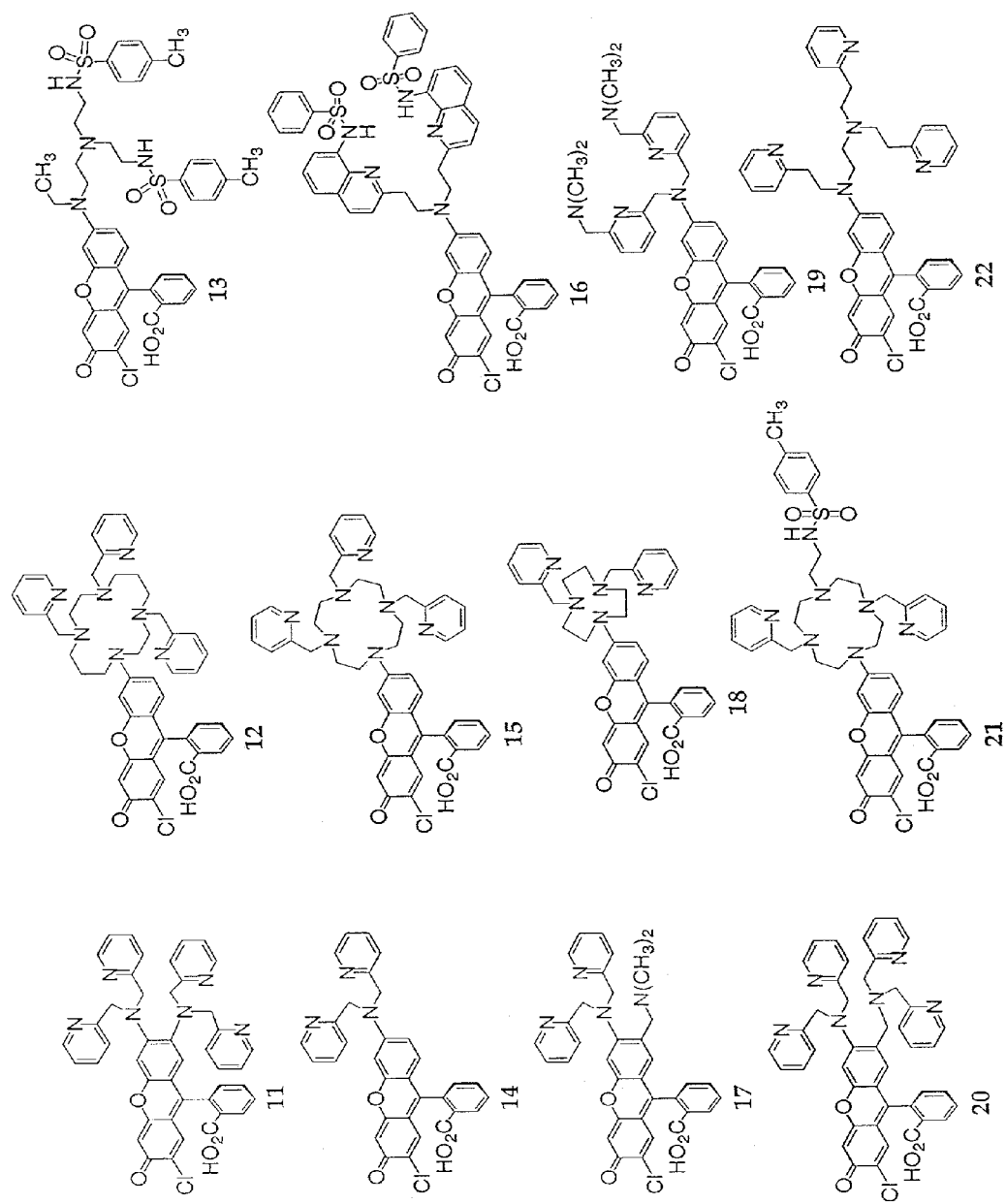
FIG. 2 depicts subject ligands of interest that are rhodafluor compounds.
Figure 3:
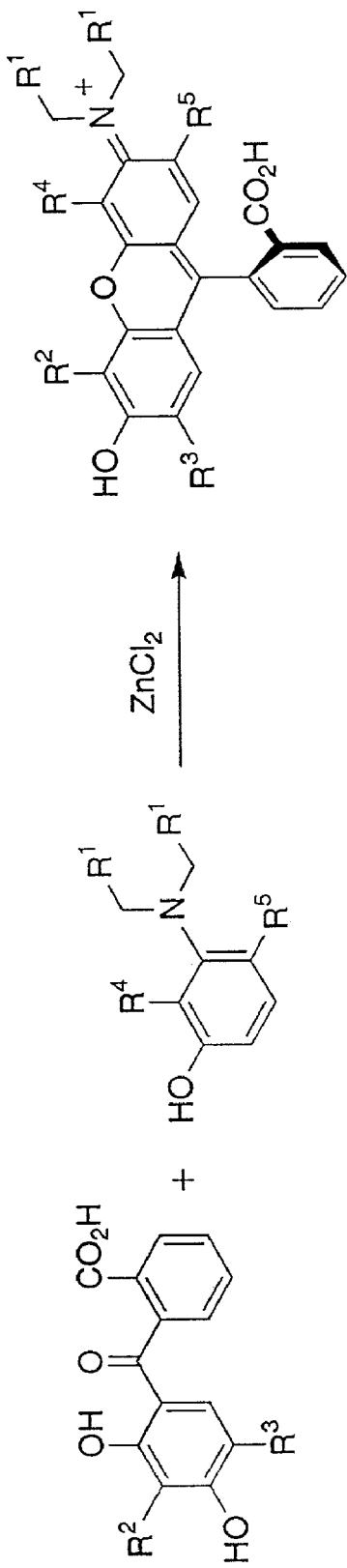
FIGS. 3–10 present different schemes for preparing the subject compounds, as described in greater detail below.

All of the subject compounds may be prepared by the methods taught herein in conjunction with methods known to those of skill in the art. By way of example, one route to the subject compounds involves the assembly of two fragments as indicated in FIG. 3. This convergent approach will provide a versatile technology for constructing sensors with different V, as depicted in FIG. 2. As described below and shown in FIG. 4, compound 30 has been prepared using this route.

Figure 5:
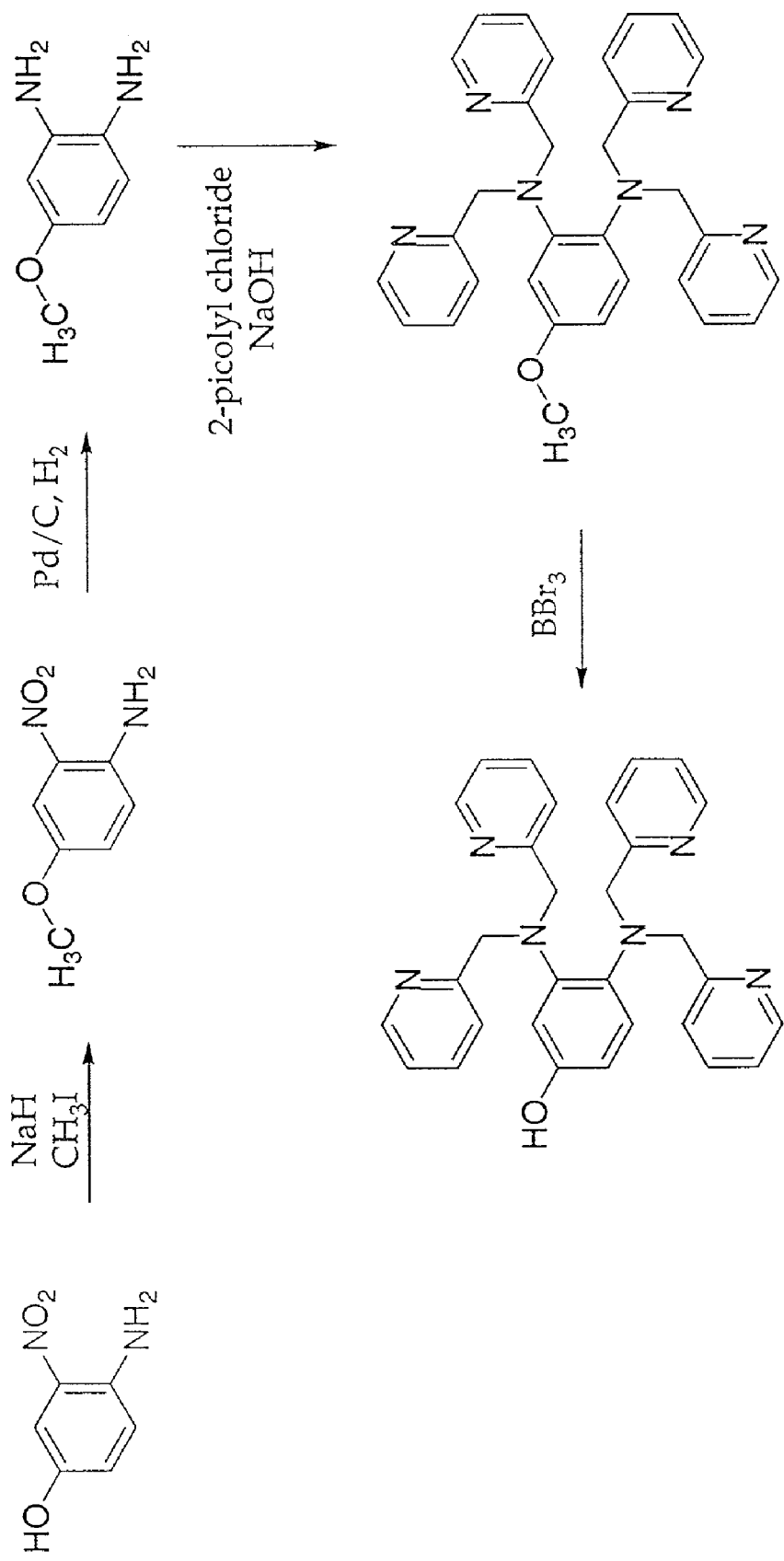

Other subject compositions of interest will incorporate a binding moiety similar to TPEN. TPEN is known to have a very high affinity and specificity for $Zn^{2+}$ over $Mg^{2+}$ and $Ca^{2+}$. The synthesis of the 3-aminophenol piece of a rhodafluor-TPEN ligand utilizes standard protecting group methodology and is similar to reported syntheses of similar compounds, as shown in FIG. 5. The resulting subject ligand prepared in the reaction depicted generally in FIG. 3 should result in a subject compound having the structure shown in Formula 2 with one —AV group in the 7' position, and is depicted as compound 11 in FIG. 2.

Figure 6:
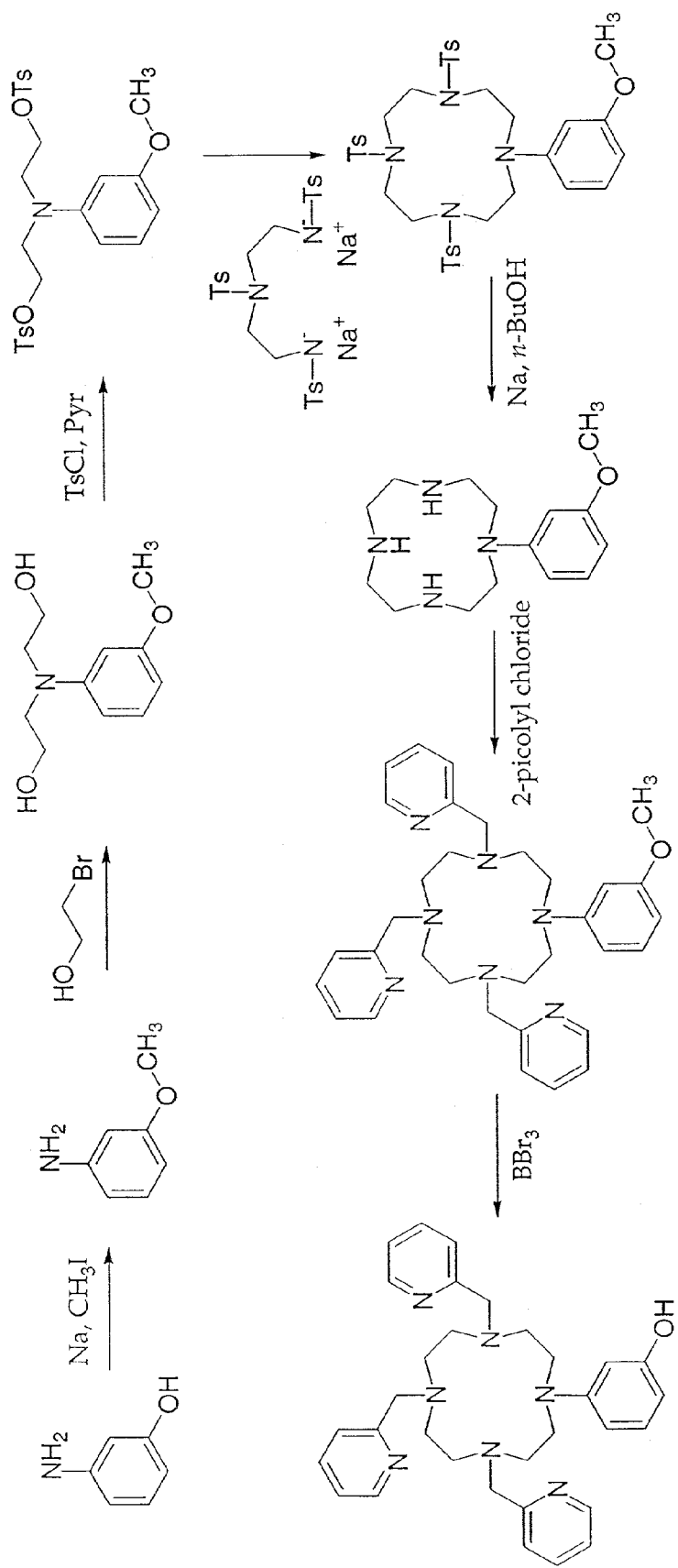
Figure 9:
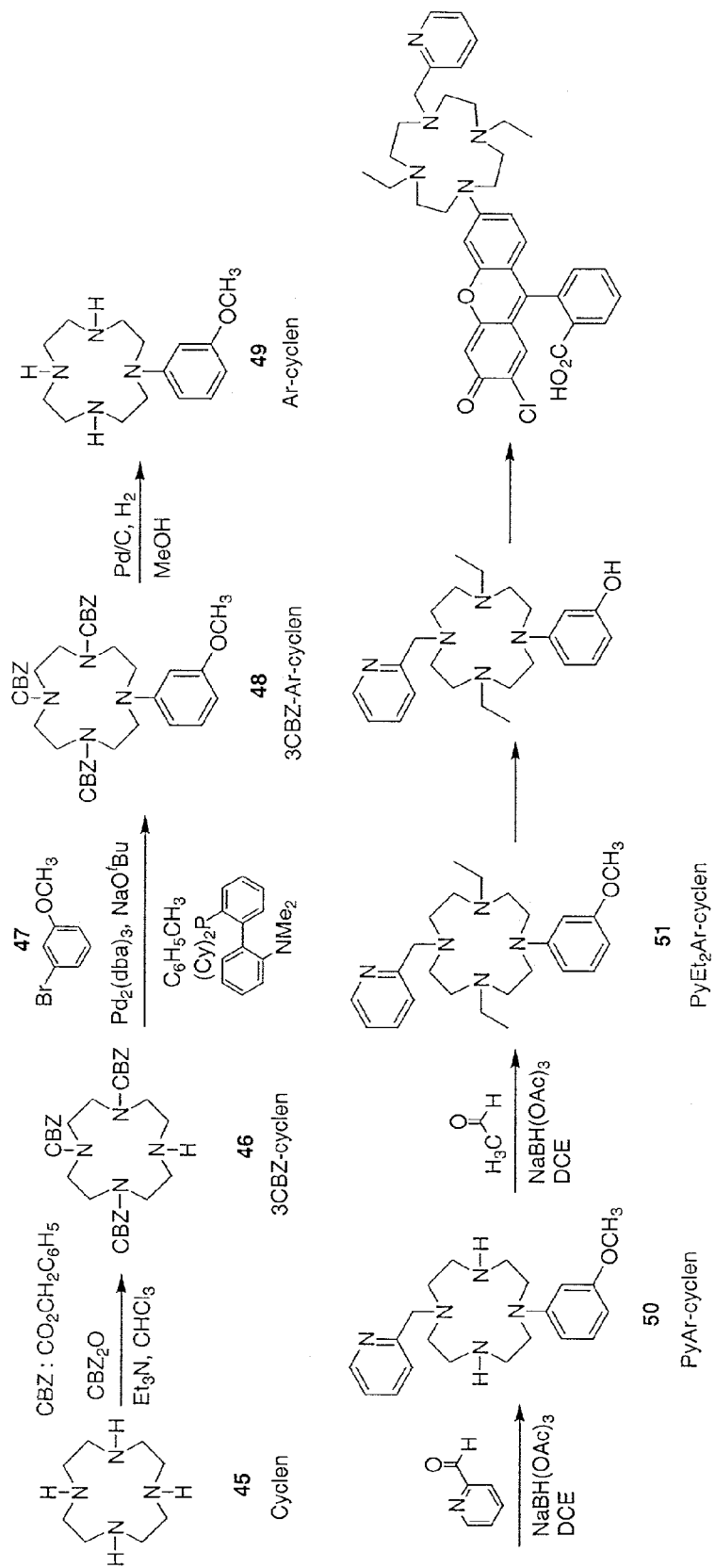

Other Lewis bases are contemplated by the present invention. For example, macrocyclic amines containing an additional sulfonamide moiety are known to be high affinity binding ligands and tertiary alkyl amines are known to be weakly binding. The proposed synthesis of a 3-aminophenol portion of a cyclen ligand containing pyridyl groups is shown in FIG. 6. It is also possible that the addition of the pyridine rings to the macrocycle should help the molecule to diffuse passively into cells. The subject composition prepared as depicted generally in FIG. 3 will have the general structure shown in Formula 3, with one variant thereof shown in FIG. 1 and as compound 15 in FIG. 2. FIG. 9 shows the preparation of a subject ligand having a bound macrocycle, with many of the various compounds having been prepared as described below.

Figure 7:
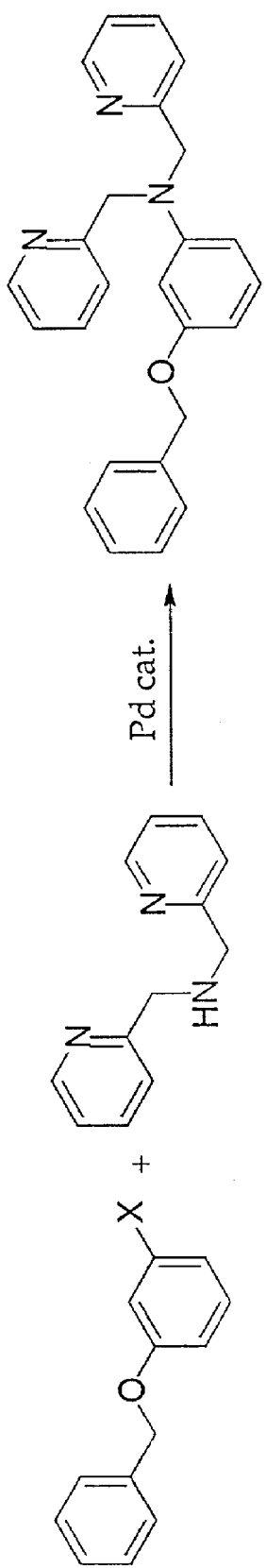

Another methodology for preparing compounds containing the Lewis bases for metal binding in FIG. 3 involves palladium catalyzed aryl amination shown in FIG. 7. By this reaction, a number of subject ligands, including many of those depicted in FIG. 2, may be synthesized. Using both the Pd-amination reactions and target-oriented organic synthesis a library of compounds will be prepared and the corresponding subject ligands examined.

As more subject ligands are prepared, high throughput screening methodologies will be useful in evaluating their fluorescent properties. A fluorescence plate reader with wells containing the individual compounds could be loaded with known quantities of a metal ion and the relative fluorescence intensity would provide a quick screening process for the fluorescent properties of the subject ligands with and without metal ion.

IV Exemplary Metal Ions

The metal atoms that may form a coordination complex with the subject ligands or used in the subject methods may be selected from those that have usually at least three, four, five, six, seven coordination sites or more. In certain embodiments, the subject ligands and methods may be used to coordinate a wide range of metal ions, including light metals (Groups IA and IIA of the Periodic Table), transition metals (Groups IB–VIIIB of the Periodic Table), posttransition metals, metals of the lanthanide series and metals of the actinide series. A non-limiting list of metal ions for which the present invention may be employed (including exemplary oxidation states for them) includes: $Li^+$, $Na^+$, $K^+$, $Mg^+$, $Ca^+$, $Zn^{2+}$, $Cd^{2+}$, $Hg^{2+}$, $Cu^{2+}$, $Pd^{2+}$, $Pt^{2+}$. In certain preferred embodiments, the subject compositions do not contain hard Lewis bases, such as carboxylates.

The design of a the subject compositions for detecting a particular metal ion will be possible by one of skill in the art, wherein issues such as selectivity, quantum yield, ease of synthesis and the like will be important criteria. By way of example, it has been observed that the fluorescence of ligands complexed to redox active transition metal ions is often quenched, and such quenching is usually attributed to EET with some contribution from the heavy atom effect and PET. Accordingly, to prepare fluorescent ligands that will serve as sensors for transition metal ions with unpaired d electrons, it will be necessary to take this affect into account.

V Fluorescence Assays (1) Instrumentation

Fluorescence of a ligand provided by the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon or Molecular Dynamics. In certain embodiments, the device is coupled to a signal amplifier and a computer for data processing.

(2) General Aspects

In general, assays using subject ligands involve contacting a sample with such a ligand and measuring fluorescence. The presence of a metal ion that interacts with the ligand may alter fluorescence of the ligand in many different ways. Essentially any change in fluorescence caused by the metal may be used to determine the presence of the metal and, optionally the concentration of the metal, in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the ligand to fluoresce. To determine the excitation spectrum for a ligand in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by metal in a sample may be used as the basis for determining the presence, and optionally, the concentration of metal in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a metal in a sample may be used to determine the presence or concentration of the metal ion in the sample. Changes in excitation or emission spectra may be measured as ratios of two wavelengths. A range of changes are possible, from about a few nms to 5, 10, 15, 25, 50, 75 100 or more nms.

Quantum yield may be obtained by comparison of the integrated area of the corrected emission spectrum of the sample with that of a reference solution. One possible reference solution is a solution of fluorescein in 0.1 N NaOH, quantum efficiency 0.95. The concentration of the reference is adjusted to match the absorbance of the test sample. The quantum yields may be calculated using the following equation.

$$\Phi_{sample} = \Phi_{standard} \times \frac{\int emission_{sample}}{\int emission_{standard}} \times \frac{Abs_{standard}}{Abs_{sample}}$$

A change in quantum yield caused by a metal ion may be used as the basis for detecting the presence of the metal in a sample and may optionally be used to determine the concentration of the metal ion. A range of changes are possible in the subject invention. For example, the difference in the quantum yield for a subject ligand in the presence of a metal ion may be about 10%, 25%, 50%, 75% the quantum yield, or it may be 2, 3, 5, 10, 100, 200, 1000, 10000 times greater or more. The same values may be used to describe changes observed in intensity in such the subject assays.

It is expected that some samples will contain compounds that compete for metal-binding with the fluorescent ligand. In such cases, the fluorescence measurement will reflect this competition. In one variation, the fluorescence may be used to determine the presence or concentration of one or more such metal binding compounds in a sample.

(3) In vitro Assays

In one variation, the presence of a metal ion in a sample is detected by contacting the sample with a subject ligand that is sensitive to the presence of the metal. The fluorescence of the solution is then determined using one of the above-described devices, preferably a spectrofluorimeter. Optionally, the fluorescence of the solution may be compared against a set of standard solutions containing known quantities of the metal. Comparison to standards may be used to calculate the concentration of the analyte, i.e. the metal ion.

The metal may be essentially any substance described above. The concentration of the metal may change over time and the fluorescent signal may serve to monitor those changes. For example, the particular form of the metal that interacts with the ligand may be produced or consumed by a reaction occurring in the solution, in which case the fluorescence signal may be used to monitor reaction kinetics.

In certain embodiments, the sample is a biological fluid, lysate, homogenate or extract. The sample may also be an environmental sample such as a water sample, soil sample, soil leachate or sediment sample. The sample may be a biochemical reaction mixture containing at least one protein capable of binding to or altering a metal. Samples may have a pH of about 5, 6, 7, 8, 9, 10, 11, 12 or higher.

(4) In vivo Assays

In another variation, the presence of a metal ion in a biological sample may be determined using a fluorescence microscope and the subject ligands. The biological sample is contacted with the fluorescent sensor and fluorescence is visualized using appropriate magnification, excitation wavelengths and emission wavelengths. In order to observe co-localization of multiple analytes, the sample may be contacted with multiple fluorescent molecules simultaneously. In certain embodiments the multiple fluorescent molecules differ in their emission and/or excitation wavelengths.

Biological samples may include bacterial or eukaryotic cells, tissue samples, lysates, or fluids from a living organism. In certain embodiments, the eukaryotic cells are nerve cells, particularly glutamate neurons. In other embodiments, the eukaryotic cells are neurons with mossy fiber terminals isolated from the hippocampus. Tissue samples are preferably sections of the peripheral or central nervous systems, and in particular, sections of the hippocampus containing mossy fiber terminals. It is also anticipated that the detection of a metal in a cell may include detection of the metal in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices.

(5) Assays using Subject Compounds

The solution or biological sample is contacted with a subject ligand, and fluorescence of the ligand is excited by light with wavelengths ranging from 340 nm to 600 nm. Light emitted by the ligand is detected by detecting light of wavelengths greater than 480 nm. In certain embodiments the excitation wavelengths range from 450 to 510 nm and the detection wavelengths are greater than 535 nm.

Exemplification

1. Chemicals and Instrumentation.

Dichloromethane ($CH_2Cl_2$), 1,2-dichloroethane (DCE) and chlorobenzene ($C_6H_5Cl$) were distilled from calcium hydride ($CaH_2$) under nitrogen. Acetonitrile ($CH_5CN$) was distilled from $CaH_2$ under nitrogen and dried over 3 Å molecular sieves. Nitrobenzene ($C_6H_5NO_2$), dimethylformamide (DMF), and ethyl acetate (EtOAc) were dried over 3 Å molecular sieves. Deuterated chloroform ($CDCl_3$) was dried over 3 Å molecular sieves. Di(2-picolyl)amine (DPA), 4',5'-dibromomethylfluorescein di-t-butyldiphenylsilyl ether (16), 2'-carboxy-5-chloro-2,4-dihydroxybenzophenone (29), and 2'-chloro-5'-methylfluorescein (19) were prepared as previously described. All other reagents were purchased and used as received. Flash column chromatography was performed with silica gel-60 (230–400 mesh) or Brockman I activated basic aluminum oxide (150 mesh). Thin layer chromatographic (TLC) analysis was performed with Merck F254 silica gel-60 plates or Merck F254 aluminum oxide-60 and viewed by UV light, or developed with ceric ammonium molybdate, ninhydrin or iodine stain. NMR spectra were recorded on a Varian 500 MHz spectrometer at ambient probe temperature, 283 K, and referenced to the internal $^1H$ and 13C solvent peaks. Electrospray ionization (ESI), and electron impact (EI) mass spectrometry were performed in the MIT Department of Chemistry Instrumentation Facility using m-nitrobenzyl alcohol as the matrix.

2. Synthesis of Subject Compositions

Figure 4:
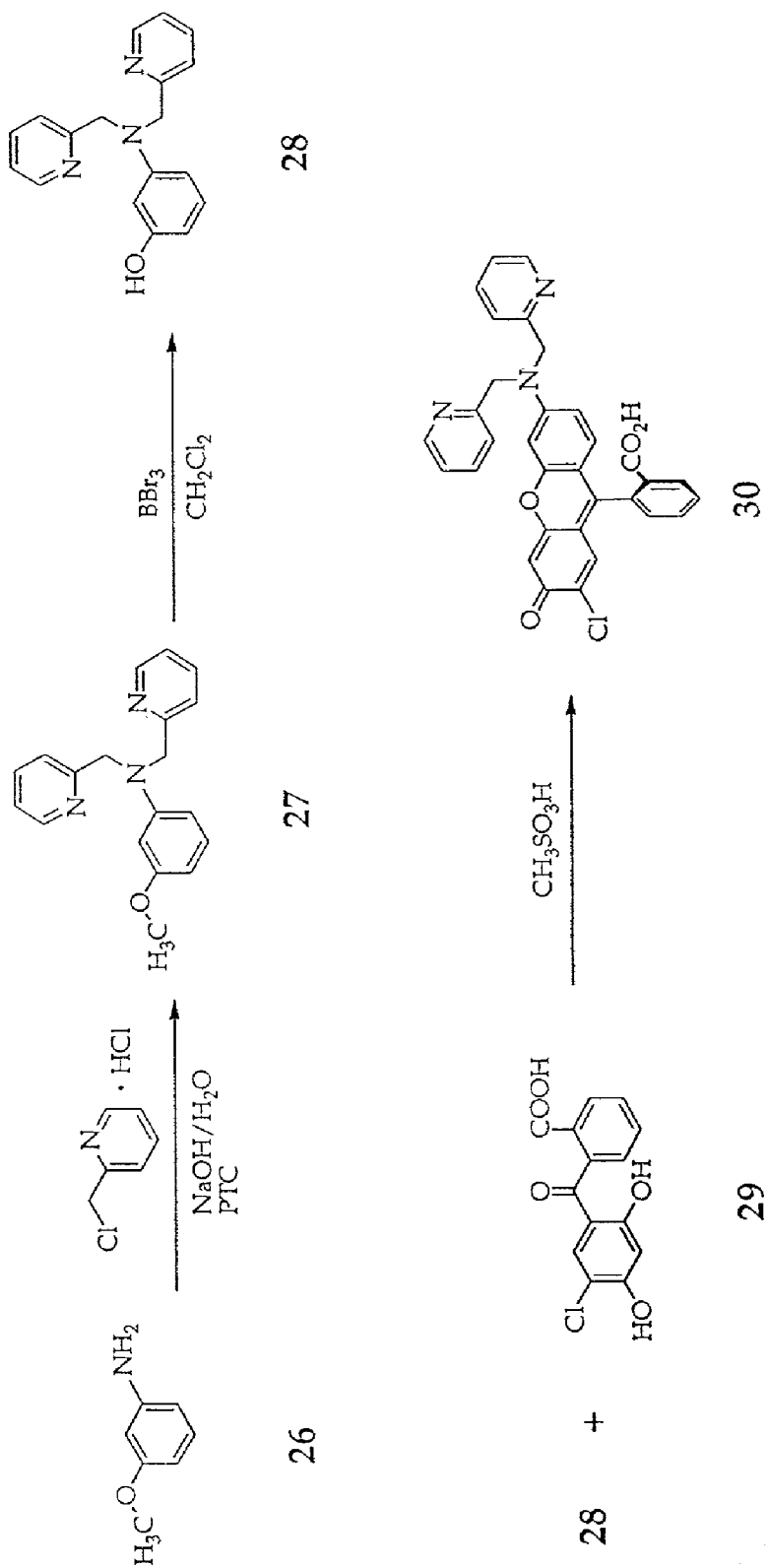

The synthesis of a subject ligand is outlined in FIG. 4. Dialkylation of m-anisidine (26) with picolyl chloride affords N,N-bis(2-pyridylmethyl)-m-anisidine (27) in fair yield. Subsequent removal of the methyl protecting group with boron tribromide ($BBr_3$) provides N,N-bis(2-pyridylmethyl)-3-aminophenol (28), one of the required fragments for the synthesis of compound 30. A variety of reagents was screened to catalyze the condensation of 28 with 2'-carboxy-5-chloro-2,4-dihydroxybenzophenone (29) to yield compound 30. Reactions in THF (200° C., sealed vessel) using $ZnCl_2$ and $AlCl_3$ failed to yield the desired product. Compound 30 was successfully isolated from the reaction of 28 and 29 in neat methane sulfonic acid ($CH_3SO_3H$). The affinity of compound 30 for $Zn^{2+}$ was found to be weak.

Figure 8:
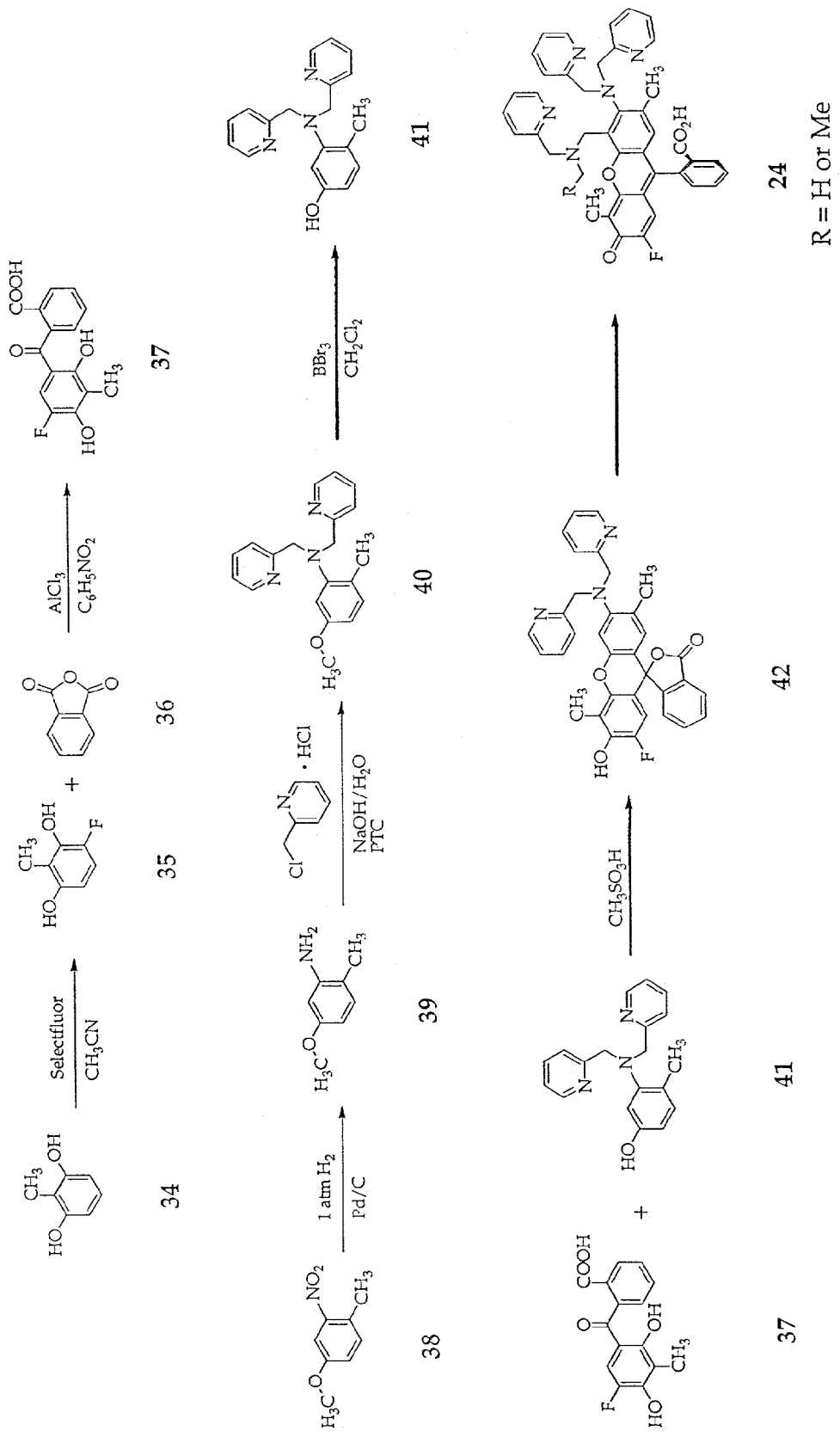

An alternative approach to synthesizing a subject ligand is depicted in FIG. 8, Assembly of the second piece of the desired compound, 2'-carboxy-5-fluoro-3-methyl-2,4-dihydroxybenzophenone (37), requires the preparation of a halogenated 2-methyl resorcinol. Fluorination of 2-methylresorcinol occurs under mild conditions using Selectfluor (1-(chloromethyl)-4-fluoro-1,4-diazoniabicyclo[2.2.2]octane bis(tetrafluoroborate)), a commercially available electrophilic fluorinating agent. The synthesis of 37 follows the identical synthesis used for the preparation of 29.

Figure 10:
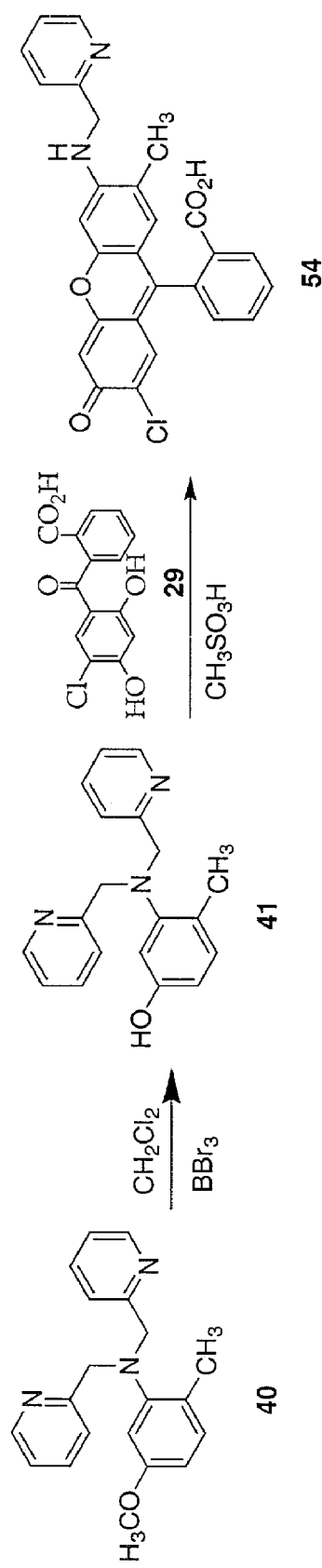

Synthesis of 4-methyl-N,N-bis(2-pyridylmethyl)-3-aminophenol (41) follows an identical route to the one used to prepare 28, as described below. Condensation of 37 and 41 should provide 42, with blocking groups in the 2', 4', and 7' positions. The fluorine at the 2' position should not only serve as a blocking group, but should also lower the $pK_a$ of the adjacent phenol and shifts the excitation and emission wavelengths to longer wavelengths. Reaction of 41 with 29 under fluorescein synthesis conditions failed to yield the desired compound (FIG. 10). An unexpected decomposition pathway results in the elimination of one of the 2-picolyl groups from the aniline nitrogen. Coupling of a ligand to the aniline nitrogen provides an alternative possibility to elaborating the structure.

Further elaboration of 42 as shown in FIG. 8 may be possible by using a Mannich reaction, or by installing an aldehyde group in the 5 position via a Vilsmeier reaction. An aldehyde at the 5 position would be useful for preparing a series of subject compounds having the general formula shown in Formula 2.

FIG. 9 outlines the synthesis of a cyclen-based 3-aminophenol and a subject ligand. Installation of protecting groups on three nitrogens restricts the Pd-coupling to a single site on the cyclen ring. The preparation of the tri-protected compound from commercially available cyclen (45) was accomplished using procedures for the preparation of analogous Boc-protected cyclens. Coupling of the 3-bromoanisidine (47) with the 3CBZ-cyclen (46) proceeds in high yield (>50%). Removal of the CBZ protecting groups occurs under mild conditions in high yield to afford Ar-cyclen (49). Reaction of 49 with 2-pyridinecarboxaldehyde under reducing conditions yields the 1,7 substituted PyAr-cyclen (50) with excellent selectivity. None of the 1,4-product is observed, and only small quantities of the compound containing a second pyridyl arm are recovered when the quantity of aldehyde is restricted to 1 equivalent. When submitted to identical reductive amination conditions using an excess of acetaldehyde, the remaining two secondary nitrogens of 50 undergo alkylation yielding the $PyEt_2Ar$-cyclen (51). Removal of the methyl-protecting group from the phenol provides the 3-aminophenol derivative. Subsequent condensation of the cyclen derivative with under analogous conditions used to prepare the other subject ligands described herein will complete the synthesis of this subject ligand. Although initial efforts to deprotect the methyl ether have not been successful, additional conditions are being examined and other protecting groups, such as a benzyl ether, will be considered. A Benzyl protecting group will be removed at the same stage as the CBZ amides by hydrogenation.

N,N-Bis(2-pyridylmethyl)-m-anisidine (27). Picolylchloride hydrochloride (12.0 g, 73.4 mmol) was dissolved in 3 mL of water, and 18 mL of 5 N NaOH was added to give a pink solution. An additional 18 mL of 5 N NaOH was added to the vigorously stirring solution, after m-anisidine (1.8 mL, 16.0 mmol) was combined with the solution of picolylchloride. An aliquot of cetyltrimethylammonium chloride (250 µL, 25 wt. % in water) was added as a phase transfer catalyst (PTC), and the reaction was stirred vigorously under Ar. Additional picolylchloride hydrochloride (5.6 g, mmol) was added to the solution after 48 h, and after 144 h, an additional portion of picolylchloride hydrochloride (10.0 g, mmol) and 15 mL of 5 N NaOH. After a total reaction time of 11 days, the product was extracted into $CH_2Cl_2$, and dried over $MgSO_4$, to give a brown solid after solvent removal. Flash chromatography on basic alumina with solvent gradient (24:1→4:1 $CH_2Cl_2$/EtOAc) yielded the product as a yellow solid (1.72 g, 35.2%). TLC $R_f$=0.33 (4:1 $CH_2Cl_2$/EtOAc). $^1$H NMR (CDCl$_3$, 500 MHz) δ3.69 (3 H, s), 4.85 (4 H, s), 6.27 (1 H, t, J=2.5 Hz), 6.30 (2 H, tt, J=2.0, 7.5 Hz), 7.08 (1 H, t, J=8.0 Hz), 7.17 (2 H, t, J=5.0 Hz), 7.31 (2 H, d, J=7.5 Hz), 7.67 (2 H, t, J=7.5 Hz), 8.61 (2 H, dd, J=1.0, 5.0 Hz). $^{13}$C NMR (CDCl$_3$, 125 MHz) δ 55.23, 57.5, 99.26, 102.29, 105.75, 120.94, 122.20, 130.19, 137.01, 148.88, 158.93, 160.94. HRMS (ESI): Calcd for MH$^+$, 306.1606; Found 306.1606.

N,N-Bis(2-pyridylmethyl)-3-aminophenol (28). A solution of N,N-Bis(2-pyridylmethyl)-m-anisidine (27, 500 mg, 1.64 mmol) in 20 mL of $CH_2Cl_2$ was frozen with liquid $N_2$, and 50 mL of 1.0 M BBr$_3$ (50 mmol) in $CH_2Cl_2$ was added via a cannula. The solution was allowed to slowly warm to room temperature, and stirred under Ar for 40 h. The reaction mixture was chilled to −40° C. via an isopropanol/dry ice bath, and MeOH was added slowly to quench the excess BBr$_3$. The quenched reaction mixture was diluted with ~300 mL of water and boiled for 45 min. After the aqueous solution was cooled, neutralized to pH ~6.5 with saturated NaHCO$_3$, and saturated with KCl, the product was extracted into $CH_2Cl_2$ to give a red solid after solvent removal. Flash chromatography on basic alumina (4:1 $CH_2Cl_2$/EtOAc) yielded the product as a yellow solid (190 mg, 39.8%). TLC $R_f$=0.27 (17:3 $CH_2Cl_2$/EtOAc). $^1$H NMR (CDCl$_3$, 500 MHz) δ4.81 (4 H, s), 6.12 (1 H, t, J=2.0 Hz), 6.23 (1 H, dd, J=2.5, 8.0 Hz), 6.30 (1H, dd, J=2.0, 8.0 Hz), 7.04(1 H, t, J=8.0 Hz), 7.11(2 H, t, J=5.0 Hz), 7.29(2 H, d, J=8.0 Hz), 7.64 (2 H, td, J=1.5, 7.5 Hz), 8.34 (2 H, d, J=4.5 Hz). $^{13}$C NMR (CDCl$_3$, 125 MHz) δ 57.28, 99.74, 104.26, 105.56, 121.19, 122.45, 130.69, 137.61, 149.06, 149.36, 158.56, 158.88. HRMS (ESI): Calcd for MH$^+$, 292.1450; Found 292.1444.

9-(o-Carboxyphenyl)-2-chloro-6-[bis(2-pyridylmethyl) amino]-3-xanthanone (30). N,N-Bis(2-pyridylmethyl)-3-aminophenol (28, 300 mg, 1.03 mmol) and 2'-carboxy-5-chloro-2,4-dihydroxybenzophenone (29, 295 mg, 1.01 mmol) were combined in 5 mL of methane sulfonic acid (CH$_3$SO$_3$H). The resulting dark red solution was stirred for 48 hrs at 70° C. The reaction mixture was diluted with 250 mL of water, chilled to 0° C., and slowly neutralized with saturated NaHCO$_3$. The aqueous mixture was extracted thoroughly with $CH_2Cl_2$, and the combined organic extracts were dried over MgSO$_4$ to give a red solid after filtration and solvent removal. Flash chromatography on silica (93:7 CHCl$_3$/MeOH) yielded the product as a red solid (322 mg, 57.1%). TLC $R_f$=0.47 (9:1 CHCl$_3$/MeOH). $^1$H NMR (CDCl$_3$, 500 MHz) δ4.84 (4 H, s), 6.43 (2 H, d, J=10.5 Hz), 6.56 (1 H, d, J=8.5 Hz), 6.73 (2 H, s), 7.14–7.24 (5 H, m), 7.56–7.69 (4 H, m), 8.02 (1 H, d, J=7.5 Hz), 8.54 (2 H, d, J=5.0 Hz). $^{13}$C NMR (CDCl$_3$, 125 MHz) δ19.86, 21.46, 56.57, 98.94, 103.81, 109.70, 111.85, 121.25, 122.88, 125.87, 126.11, 128.23, 128.78, 128.99, 129.41, 129.66, 129.93, 129.99, 134.20, 137.98, 149.35, 153.01, 157.20, 169.35. HRMS (ESI): Calcd for MH$^+$, 548.1377; Found 548.1372.

4-[Bis(2-pyridylmethyl)aminomethyl]-resorcinol (32). DPA (144 mg, 0.723 mmol), 2,4-dihydroxybenzaldehyde (31, 100 mg, 0.723 mmol) and NaBH(OAc)$_3$ (300 mg, 1.41 mmol) were combined in 25 mL of DCE and stirred under Ar for 24 h. The reaction mixture chilled to 0° C. and quenched by the addition of 10 mL of saturated NaHCO$_3$. The crude product was extracted into $CH_2Cl_2$, and dried over MgSO$_4$ to give a yellow solid after solvent removal. Flash chromotography on basic alumina (9:1 CHCl$_3$/MeOH) yielded the product as a white solid (66 mg, 28%). TLC $R_f$=0.34 (19:1 CHCl$_3$/MeOH). $^1$H NMR (CDCl$_3$, 500 MHz) δ3.72 (2 H, s), 3.88 (4 H, s), 6.27 (1 H, dd, J=2.5, 8.0 Hz), 6.45 (1 H, d, J=2.5 Hz), 6.91 (1 H, d, J=8.5 Hz), 7.17 (2 H, t, J=5.0 Hz), 7.35 (2 H, d, J=8.0 Hz), J=1.5, 7.5 Hz),7.63 (2 H, td, J=1.5, 8.0 Hz), 8.57 (2H, d, J=5.0 Hz).

4-Fluoro-2-methylresorcinol (35). Selectfluor™ (11.65 g, 32.88 mmol) and 2-methylresorcinol (34, 4.09 g, 32.9 mmol) were refluxed in CH$_3$CN (300 mL) for 48 h. After ~250 mL of CH3CN was removed, the reaction mixture was diluted with water (350 mL) and extracted thoroughly with Et$_2$O. The combined organic extracts were washed successively with saturated NaHCO$_3$ solution (100 mL), saturated brine (100 mL), and water (100 mL), and dried over MgSO$_4$ to give a yellow solid after solvent removal. Flash chromatography on basic alumina with a solvent gradient (17:1 hexanes/EtOAc→4:1 hexanes/EtOAc→3:1 hexanes/EtOAc) yielded the product as a yellow solid (1.94 g, 41.4%). TLC $R_f$=0.37 (3:1 hexanes/EtOAc). $^1$H NMR (CDCl$_3$, 500 MHz) δ2.17 (3 H, s), 5.1 (2H, bs), 6.29 (1 H, q, J=4.5 Hz), 6.79 (1 H, t, J=9.0 Hz). $^{13}$C NMR (CDCl$_3$, 125 MHz) δ 8.60, 26.29, 106.10, 108.01, 111.99, 112.15, 113.15, 126.76, 142.34, 142.46, 145.25, 147.07, 150.38, 150.40, 154.84. HRMS (EI): Calcd for M$^+$, 142.0430; Found 142.0425.

2'-Carboxy-5-fluoro-3-methyl-2,4-dihydroxybenzophenone (37). Phthalic anhydride (36, 1.95 g, 13.2 mmol) and 4-fluoro-2-methylresorcinol (35, 1.84 g, 12.94 mmol) were combined in $C_6H_5NO_2$ (150 mL) and chilled to 0° C. Aluminum chloride (AlCl$_3$, 3.50 g, 26.2 mmol) added slowly over one hour and the slurry was stirred overnight while warming to room temperature. The reaction mixture was heated to 150° C. for 6 h, and the reaction mixture was diluted with 0.1 M HCl (700 mL) and hexanes (100 mL) to precipitate a black byproduct which was discarded. The hexanes and $C_6H_5NO_2$ were removed to give a black oil. The oil was filtered through silica (4:1 CHCl$_3$/MeOH) to give a black solid after solvent removal. The product was recrystallized twice (1:1 CH$_3$OH/water), washed with ice cold water and dried to give the product as an orange brown crystalline solid (0.914 g, 24.4%). TLC $R_f$=0.23 (9:1 CHCl$_3$/MeOH). $^1$H NMR (CD$_3$OD) δ 2.14 (3 H, s), 6.54 (1 H, d, J=10.5 Hz), 7.38 (1 H, dd, J=1.0, 7.5 Hz), 7.64 (1 H, td, J=1.5, 7.5 Hz), 7.71 (1 H, td, J=1.5, 7.2 Hz), 8.11 (1 H, dd, J=1.5, 7.5 Hz). $^{13}$C NMR(CDCl$_3$, 125 MHz) δ 8.12, 8.14, 112.58, 112.63, 115.38, 115.64, 115.80, 128.67, 130.74, 131.00, 131.69, 133.67, 134.18, 141.81, 144.99, 146.84, 152.28, 152.41, 160.54, 168.77, 202.84. HRMS (ESI): Calcd for MH$^+$, 291.0669; Found 291.0663.

4-Methyl-m-anisidine (39). 4-Methyl-3-nitroanisole (38, 5.40 g, 32.3 mmol) and Pd/C (0.50 g, 10% activated) were combined in 200 mL of MeOH and stirred under a hydrogen atmosphere (1 atm) for 60 h. Additional portions of Pd/C (0.5 g) were added after 12 and 36 h. The reaction mixture was filtered through celite to give a dark yellow oil after solvent removal. Flash chromatography silica (4:1 hexanes/EtOAc) yielded the product as a light brown solid (3.70 g, 83.5%). TLC R$_f$=0.27 (4:1 hexanes/EtOAc). $^1$H NMR (CDCl$_3$, 500 MHz) δ2.24 (3 H, s), 3.86 (2 H, s), 3.87 (3 H, s), 6.42 (1 H, d J=2.5 Hz), 6.49 (1 H, dd, J=2.5, 8.0 Hz), 7.12 (1 H, d, J=8.5 Hz). $^{13}$C NMR (CDCl$_3$, 125 MHz) δ15.96, 54.53, 100.38, 103.02, 114.29, 130.59, 145.61, 158.61. HRMS (EI): Calcd for M$^+$, 137.0941; Found 137.0835.

N,N-Bis(2-pyridylmethyl)-4-methyl-m-anisidine (40). Picolylchloride hydrochloride (10.0 g, 61.0 mmol) was dissolved in 3 mL of water, and 18 mL of 5 N NaOH was added to give a pink solution. An additional 18 mL of 5 N NaOH was added to the vigorously stirring solution, and 4-methyl-m-anisidine (39) (3.70 g, 27.0 mmol) was combined with the solution of picolylchloride. An aliquot of cetyltrimethylammonium chloride (450 µL, 25 wt. % in water) was added as a phase transfer catalyst (PTC), and the reaction was stirred vigorously under Ar. Additional picolylchloride hydrochloride (10.0 g, 61.0 mmol) and 5 mL of 5.0 N NaOH was added to the solution after 72 h. After 96 h, an additional portion of picolylchloride hydrochloride (6.00 g, 36.6 mmol) was added to the solution, and after 216 h a final addition of picolylchloride hydrochloride (7.00 g, 42.7 mmol) and 5 mL of 5 N NaOH was made. After a total reaction time of 11 days, the product was extracted into CH$_2$Cl$_2$, and dried over MgSO$_4$, to give a dark red oil after solvent removal. Flash chromatography on basic alumina with solvent gradient (9/1 CH$_2$Cl$_2$/EtOAc→4/1 CH$_2$Cl$_2$/EtOAc) yielded the product as a orange oil (1.43 g, 16.6%). TLC R$_f$=0.29 (4:1 CH$_2$Cl$_2$/EtOAc). $^1$H NMR (CDCl$_3$, 500 MHz) δ2.39 (3 H, s) 3.65 (3 H, s), 4.37 (4 H, s), 6.50 (1 H, dd, J=2.5, 8.5 Hz), 6.61 (1 H, d, J=3.0 Hz), 7.07–7.12 (3 H, m), 7.42 (2 H, d, J=8.0 Hz), 7.58 (2 H, td, J=2.0, 7.5 Hz), 8.52 (2 H, dt, J=1.0, 5.5 Hz). $^{13}$C NMR (CDCl$_3$, 125 MHz) δ 18.17, 55.41, 56.70, 108.09, 108.84, 122.09, 122.36, 125.05, 131.89, 136.60, 149.26, 150.22, 158.35, 159.05.

N,N-Bis(2-pyridylmethyl)-3-amino-4-methylphenol (41). A solution of N,N-bis(2-pyridylmethyl)-4-methyl-m-anisidine (40) (1, 1.00 g, 3.13 mmol) in 10 mL of CH$_2$Cl$_2$ was frozen with liquid N$_2$, and 90 mL of 1.0 M BBr$_3$ (90 mmol) in CH$_2$Cl$_2$ was added via a cannula. The solution was allowed to slowly warm to room temperature, and stirred under Ar for 40 h. The reaction mixture was chilled to –40° C. via an isopropanol/dry ice bath, and MeOH was added slowly to quench the excess BBr$_3$. The quenched reaction mixture was diluted with ~350 mL of water and boiled for 45 min. After the aqueous solution was cooled, neutralized to pH ~6.5 with saturated NaHCO$_3$, and saturated with NaCl, the product was extracted into CH$_2$Cl$_2$ to give a red solid after solvent removal. Flash chromatography on basic alumina (19:1 CHCl$_3$/MeOH) yielded the product as a yellow solid (449 mg, 47.0 %). TLC R$_f$=0.26 (19:1 CHCl$_3$/MeOH). $^1$H NMR (CDCl$_3$, 500 MHz) δ 2.38 (3 H, s), 4.33 (4 H, s), 6.49 (1 H, dd, J=2.5, 7.5 Hz), 6.60 (1 H, d, J=2.5), 7.04 (1 H, d, J=8.0 Hz), 7.10 (2 H, dd, J=5.0, 7.0 Hz), 7.45 (2 H, d, J=7.5 Hz), 7.60 (2 H, td, J=1.5, 7.5 Hz), 8.38 (2 H, dt, J=1.0, 5.0 Hz). $^{13}$C NMR (CDCl$_3$, 125 MHz) δ 18.15, 59.32, 108.94, 111.42, 122.32, 122.43, 123.95, 132.38, 137.15, 148.77, 149.64, 155.87, 158.87. FTIR (NaCl plate) 3422, 1610, 1599, 1531, 1474, 1343, 1293, 1248, 1203, 751. HRMS (ESI): Calcd for MH$^+$, 306.1601; Found 306.1614.

9-(o-Carboxyphenyl)-2-chloro-6-[(2-pyridylmethyl)amino]-3-xanthanone (54). N,N-Bis(2-pyridylmethyl)-3-amino-4-methylphenol (2,284 mg, 0.93 mmol) and 2'-carboxy-5-chloro-2,4-dihydroxybenzophenone (3,272 mg, 0.93 mmol) were combined in 5 mL of methane sulfonic acid (CH$_3$SO$_3$H). The resulting dark red solution was stirred for 48 hrs at 70° C. The reaction mixture was diluted with 250 mL of water, chilled to 0° C., and slowly neutralized with saturated NaHCO$_3$. The aqueous mixture was extracted thoroughly with CH$_2$Cl$_2$, and the combined organic extracts were dried over MgSO$_4$ to give a red solid after filtration and solvent removal. Flash chromatography on silica (9:1 CHCl$_3$/MeOH) yielded the product as a red solid (149 mg, 34.1%). TLC R$_f$=0.15 (9:1 CHCl$_3$/MeOH). $^1$H NMR (CDCl$_3$, 500 MHz) δ2.09 (3 H, s), 4.50 (2 H, s), 6.34 (1 H, s) 6.47 (1 H, s), 6.78 (2 H, s), 7.18 (1 H, d, J=7.5 Hz), 7.27 (2 H, m), 7.33 (1 H, d, J=7.0 Hz), 7.64–7.72 (3 H, m), 8.10 (1 H, d, J=8.0 Hz), 8.61 (1 H, d, J=4.5 Hz). HRMS (ESI): Calcd for MH$^+$, 471.1112; Found 471.1219.

1,4,7-Tris(benzyloxycarbonyl)-1,4,7,10-tetraazacyclododecane (3CBZ-cyclen 46). Cyclen (45, 2.00 g, 11.6 mmol) and Et$_3$N (5.2 mL) were dissolved in 300 mL of CHCl$_3$. Dibenzyl dicarbonate (5.0 g, 17.5 mmol) was dissolved in 200 mL of CHCl$_3$ and added dropwise to the stirring solution of cyclen over 10 h. The reaction mixture was stirred for 24 h at room temperature. The CHCl3 was removed, and flash chromatography on silica (3:17 hexanes/EtOAc) yielded the product as a white solid (1.70 g, 25.5%). TLC R$_f$=0.35 (EtOAc). $^1$H NMR (CDCl$_3$, 500 MHz) δ 0.91 (1 H, s), 2.76–2.87 (4 H, m), 3.29–3.77 (12 H, m), 4.88 (1 H, s), 5.05 (2 H, s), 5.14 (1 H, s), 7.18–7.34 (15 H, m). $^{13}$C NMR (CDCl$_3$, 125 MHz) δ45.43, 48.39, 48.69, 49.06, 49.26, 50.50, 50.95, 51.18, 66.63, 66.85, 66.97, 67.10, 127.54, 127.63, 127.74, 127.91, 128.04, 128.31, 128.37, 128.44, 136.58, 136.66, 136.88, 155.85, 156.20, 156.34. HRMS (ESI): Calcd for MH$^+$, 575.2870; Found 575.2868.

1,4,7-Tris(benzyloxycarbonyl)-10-(3-methoxyphenyl)-1,4,7,10-tetraazacyclo-dodecane (3CBZ-Ar-cyclen, 48). 2-Dicyclohexylphosphino-2'-(N,N-dimethyl-amino)biphenyl (3.6 mg, 9.16 µmol), Pd$_2$(dba)$_3$ (1.4 mg, 1.53 µmol) and sodium tert-butoxide (20.5 mg, 1.74 mmol) were combined in a Schlenk tube outfitted with a Teflon screwcap and dried in vacuo for 1 h. Dried 100 mg of 6 (174 µmol) was transferred into the tube in 1 mL of C$_6$H$_5$CH$_3$ while purging with Ar. To the combined materials, 3-bromoanisidine (7, 19 mL, 153 µmol) was added via a syringe. After thoroughly purging with Ar, the tube was sealed and placed in oil bath at 80° C. and stirred for 36 h. The reaction mixture was cooled, diluted with CH$_2$Cl$_2$, filtered through celite, and the solvent was removed. Flash chromatography on silica (1:1 hexanes/EtOAc) yielded the product as a white solid (102 mg, 51%). TLC R$_f$=0.60 (EtOAc). $^1$H NMR (CDCl$_3$, 500 MHz) δ 3.35 (16 H, bs), 3.73 (3 H, s), 5.02 (2 H, s), 5.11 (4 H, s), 6.28 (2 H, s), 6.40 (1 H, d, J=7.5 Hz), 7.10 (1 H, t, J=8.0 Hz), 7.27–7.31 (15 H, m). $^{13}$C NMR (CDCl$_3$, 125 MHz) δ 50.06, 50.54, 55.21, 67.15, 67.37, 128.08, 128.14, 128.31, 128.41, 128.60, 128.67, 130.27, 136.54, 136.76, 160.75. HRMS (ESI): Calcd for MH$^+$, 681.3288; Found 681.3307.

1-(3-methoxyphenyl)-1,4,7,10-tetraazacyclo-dodecane (Ar-cyclen, 49). Pd/C (500 mg, 10% activated) and 3CBZ-Ar-cyclen (8, 785 mg, 1.15 mmol) were combined in 125 mL of MeOH and stirred under a hydrogen atmosphere (1 atm) for 24 h. The reaction mixture was filtered through celite to give a dark yellow oil after solvent removal. Flash chromatography on silica (72:25:3 $CHCl_3/MeOH/NH_4OH$) yielded the product as a white solid (304 mg, 95%). TLC $R_f$=0.24 (97:3 $CHCl_3$/MeOH). $^1H$ NMR ($CDCl_3$, 500 MHz) δ 2.52 (3 H, s), 2.63 (4 H, t, J=5.0 Hz), 2.83 (4 H, t, J=5.0 Hz), 2.87 (4 H, J=5.0 Hz), 3.48 (4 H, t, J=5.0 Hz), 3.76 (3 H, s), 6.31–6.38 (2 H, m), 6.46 (1 H, dd, J=2.0, 8.0 Hz), 7.10–7.15 (1 H, m). $^{13}C$ NMR ($CDCl_3$, 125 MHz) δ47.04, 47.10, 47.19, 52.54, 55.34, 101.99, 103.134, 129.94, 130.11, 150.90, 160.67. HRMS (ESI): Calcd for $MH^+$, 279.2179; Found 279.2172.

1-(3-methoxyphenyl)-7-(2-pyridylmethyl)-1,4,7,10-tetraazacyclo-dodecane (PyAr-cyclen, 50). Ar-cyclen (9, 300 mg, 1.08 mmol) and 2-pyridinecarboxaldehyde (128 μL, 136 mmol) were combined in 30 mL DCE and stirred. Sodium triacetoxyborohydride (318 mg, 1.50 mmol) was added and the reaction mixture was stirred for 24 h at room temperature. Saturated $NaHCO_3$ (15 mL) was added to quench unreacted borohydride reagent. The aqueous layer was extracted with EtOAc. The combined organic layers were washed with saturated brine, dried over $MgSO_4$, filtered, and the solvent was removed. Flash chromatography on silica with a solvent gradient (90:9:1 $CHCl_3/MeOH/NH_4OH$→20:4:1 $CHCl_3/MeOH/NH_4OH$) yielded the product as a white solid (154 mg, 31.0%). TLC $R_f$=0.59 (10:4:1 $CHCl_3$/MeOH/$NH_4OH$). $^1H$ NMR ($CDCl_3$, 300 MHz) δ 2.54–2.56 (4 H, m), 2.62–2.65 (4 H, m), 2.74 (4 H, t, J=5.1 Hz), 3.37 (4 H, t, J=4.8 Hz), 3.67 (2 H, s), 3.73 (3 H, s), 6.36 (1 H, dd, J=2.4, 8.1 Hz), 6.50 (1 H, t, J=2.4 Hz), 6.60 (1 H, dd, J=2.4, 8.1 Hz), 6.93–6.98 (2 H, m), 7.10–7.24 (2 H, m), 8.24 (1 H, dd, J=0.6, 3.9 Hz). $^{13}C$ NMR ($CDCl_3$, 75 MHz) δ 47.01, 47.24, 52.45, 53.14, 55.21, 62.27, 102.27, 103.37, 109.15, 122.00, 122.87, 129.72, 136.65, 148.71, 152.03, 159.75, 160.52. HRMS (ESI): Calcd for $MH^+$, 370.2607; Found 370.2614.

1-(3-Methoxyphenyl)-4,10-(diethyl)-7-(2-pyridylmethyl)-1,4,7,10-tetraazacyclo-dodecane ($PyEt_2Ar$-cyclen, 51). $PyEt_2Ar$-cyclen (10, 154 mg, 334 μmol) and acetaldehyde (5 mL, 90 mmol) were combined at 0° C. in 20 mL DCE and stirred. The temperature of the reaction mixture was maintained between 0–20° C. to prevent evaporation of acetaldehyde. Sodium triacetoxyborohydride (600 mg, 2.83 mmol) was added, and the reaction mixture was stirred for 24 h. Saturated $NaHCO_3$ (15 mL) was added to quench unreacted borohydride reagent. The aqueous layer was extracted with EtOAc. The combined organic layers were washed with saturated brine, dried over $MgSO_4$, filtered, and the solvent was removed. Flash chromatography on silica with a solvent gradient (20:4:1 $CHCl_3/MeOH/NH_4OH$) yielded the product as a white solid (154 mg, 31.0%). TLC $R_f$=0.55 (10:4:1 $CHCl_3/MeOH/NH_4OH$). $^1H$ NMR ($CDCl_3$, 300 MHz) δ 0.93 (6 H, t, J=7.2 Hz), 2.42 (4 H, q, J=7.2 Hz), 2.56-2.63 (8 H, m), 2.78 (4 H, t, J=5.7 Hz), 3.55 (4 H, t, J=6.0 Hz), 3.66 (2 H, s), 3.75 (3 H, s), 6.10–6.19 (2 H, m), 6.26 (1 H, d, J=9.6 Hz), 7.00–7.13 (2 H, m), 7.51–7.61 (2 H, m), 8.46 (1 H, d, J=4.8 Hz). HRMS (ESI): Calcd for $MH^+$, 426.3233; Found 426.3227.

3. Measurements of Fluorescent Properties of the Subject Ligands

The following methods are presented for measuring the spectroscopic properties of the subject compositions with the metal ion $Zn^{2+}$ and using exemplary wavelengths. Other metal ions, as described above, and other wavelengths appropriate for the subject ligand of interest, may be used in these methods by those of skill in the art without undue experimentation.

General Spectroscopic Methods. Utrol grade HEPES (2[4-(2-hydroxyethyl)-1-piperazinyl]ethane-sulfonic acid) and PIPES (piperazine-N,N'-bis(2-ethanesulfonic acid)) from Calbiochem and KCl (99.997%) may be purchased. All buffers may be filtered through 0.2 μM cellulose filters before measurements. Except for the fluorescence titration experiment, Zn solutions may be prepared by the addition of appropriate amounts of 1.0 M, 100 mM, 10 mM or 1 mM $Zn^{2+}$ stocks that were checked by atomic absorption spectroscopy for concentration accuracy, or by titration with terpyridine and measurement of the absorption spectra. The $Zn^{2+}$ stocks may be prepared from 99.999% pure $ZnCl_2$. The purity of a ligand will be verified to be greater than 99% by HPLC. The graphs may be manipulated and equations may be calculated using Kaleida graph 3.0. The pH of solutions may be recorded with a glass electrode that was calibrated prior to each use.

Fluorescence Spectroscopy. Fluorescence spectra may be recorded on a Hitachi F-3010 spectrofluorimeter under the control of a Pentium-based PC running the SpectraCalc software package. Excitation may be provided by a 150 W Xe lamp (Ushio Inc.) operating at a current of 5 A. All spectra may be normalized for excitation intensity via a rhodamine quantum counter, and emission spectra may be normalized by the manufacturer-supplied correction curves. Spectra may be routinely acquired at 25° C., maintained by a circulating water bath in 1 cm×1 cm quartz cuvettes using 3 nm slit widths and a 240 nm/min scan speed. Fluorescence emission measurements may also be acquired in a 1 cm×1 cm quartz cell using a Spex fluorolog-2 instrument with 1 nm bandwidth slits. All spectra will be corrected for emission intensity using the manufacturer-supplied photomultiplier curves. Spectra may be routinely acquired at 25° C., maintained by a circulating water bath.

UV-Visible Spectroscopy. Absorption spectra may be recorded on a Hewlett Packard 8453A diode array spectrophotometer under the control of a Pentium II-based PC running the Windows NT ChemStation software package, or a Cary 1E scanning spectrophotometer under the control of a Pentium PC running the manufacturer supplied software package. Spectra were routinely acquired at 25° C., maintained by a circulating water bath in 1 cm path length quartz cuvettes with a volume of 1.0 or 3.5 mL.

pH Dependent Fluorescence. The apparent fluorescence $pK_a$ may be measured by plotting the integrated area of the emission spectrum against the pH recorded from pH=12.5–2.5. A 1 μM solution of a subject compound (10 mLs) containing ~1 mM KOH and 100 mM KCl may be adjusted to pH 12.5 and the UV-vis and fluorescence spectra may be recorded. The pH may be lowered in steps of ΔpH=0.5 with the addition of appropriate amounts of 6 N, 2 N, 0.5 N, 1 N, 0.1 N and 0.01 N HCl recording the absorption and emission spectra at each pH interval. The volume of the solution may be controlled so the overall change in volume was <2%. Emission for a subject ligand may be integrated from 500 to 700 nm or other appropriate window. The resulting integrated emission areas may be normalized, plotted against pH, and fit with the following nonlinear equation to calculate the $pK_a$ values.

$$\Delta F = \frac{\Delta F_{1max}}{(1+e^{((pK_{a1}-mpH))})} + \frac{\Delta F_{2max}}{(1+e^{((pK_{a2}-qpH))})}$$

Job plot. The stoichiometry of the subject metal:ligand complexes may be examined using Jobs method beginning with 10.0 mL of 10 µM of the subject ligand in a 10 mM PIPES and 100 mM KCl, pH=7.0. The initial $Zn^{2+}$ free spectrum will be recorded and then to reach n µM $ZnCl_2$ (n=1–10) aliquots of 10.0/(11−n) mL will be removed and discarded iteratively and will be replaced with equal volumes of 10 µM $ZnCl_2$ in 10 mM PIPES and 100 mM KCl, pH=7.0 to vary the mole fraction of the ligand to metal. After the absorption spectra are recorded, the excess absorption (ΔAbs) may be calculated and plotted against an appropriate wavelength against the mole fraction (X).

Quantum Yield. The quantum yields of fluorescence may be obtained by comparison of the integrated area of the corrected emission spectrum of the sample with that of a reference solution, such as a solution of fluorescein in 0.1 N NaOH, quantum efficiency 0.95. The concentration of the reference will be adjusted to match the absorbance of the test sample. The quantum efficiency of the metal free ligand will be measured using dilute sample of the subject ligand in 10 mM PIPES, 100 mM KCl and 50 µM EDTA, pH=7.0. The quantum efficiency of the metal bound ligand will be measured using a dilute sample of the subject ligand in 10 mM PIPES, 100 mM KCl and 100 µM $ZnCl_2$, pH=7.0. Emission for the subject ligand will be integrated from 496 to 600 nm or other appropriate window with excitation at 492 nm or another suitable wavelength. The quantum yields will be calculated with the following equation.

$$\Phi_{sample} = \Phi_{standard} \times \frac{\int emission_{sample}}{\int emission_{standard}} \times \frac{Abs_{standard}}{Abs_{sample}}$$

Fluorescence $Zn^{2+}$ Binding Titration ($K_{d1}$). The first $K_d$ associated with $Zn^{2+}$ binding will be measured by a fluorescence titration as described previously. Spectra of the subject ligand will be acquired by exciting at 490 nm or other suitable wavelength and collecting and integrating from 500–575 nm or other appropriate window. The measurements will be performed in triplicate to ensure accuracy of the $K_d$ value.

References

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Anderegg et al. *Helv. Chim. Acta* 1977, 60: 123–140
Atar, et al. *J. Biol. Chem.* 1995, 270: 2473–2477
Belgodere et al. *Heterocycles* 1985, 23, 349–354.
Buchen et al. *J. Chem. Soc., Dalton Trans.* 1997, 2697–2703.
Budde et al. *Neuroscience* 1997, 79, 347–358.
Budde et al. *Neuroscience* 1997, 79: 347–358
Burton et al. *J. Soc. Chem. Ind. London* 1948: 67: 345
Canzoniero et al. *Neurobiology of Disease* 1997, 4, 275–279.
Choi et al. *Ann. Rev. Neurosci.* 1998, 21: 347–375
Copeland et al. *J. Am. Chem. Soc.* 1999, 121, 4306–4307.
Cuajungco et al. *Neurobiology of Disease* 1997, 4: 137–169
Czarnik, A. W. *Curr. Biol.* 1995, 2: 423–428
da Mota et al. *J. Chem. Soc. (A)* 1969, 2036–2042.
de Silva et al. *Chem. Rev.* 1997, 97: 1515–1566
Ebadi, et al. *Methods Enzymol.* 1991, 205: 363–387
Ebadi, et al. *J. Neurochem.* 1996, 66: 2121–2127
Ebadi, et al. *Neurochem. Int.* 1995, 27: 1–22
Evans, I. *J. Org. Chem.* 1959, 24: 863
Fahrni et al. *J. Am. Chem. Soc.* 1999, 121, 11448–11458.
Feig et al. *Inorg. Chem.* 1996, 25: 6892–6898
Frederickson et al. *Biol. Signals* 1994, 3: 127–139
Frederickson et al. *J. Neurosci. Meth.* 1987, 20, 91–103.
Frederickson, C. *Int. Rev. Neurobiol.* 1989, 31: 145–238
Frederickson, et al. *J. Neurosci. Meth.* 1987, 20: 91–103
Gruenwedel, D. W. *Inorg. Chem.* 1968, 7: 495–501
Harrison et al. *Neuropharmacology* 1994, 33: 935–952
Hartwig et al. *Acc. Chem. Res.* 1998, 31, 852–860.
Hirano et al. *Angew. Chem. Int. Ed.* 2000, 39, 1052–1054.
Höbrlein, U. *Chemische Berichte* 1954, 87, 463–472.
Houser et al. *J. Am. Chem. Soc.* 1995, 117, 10745–10746.
Huang, E. *Proc. Natl. Acad. Sci. U.S.A.* 1997, 94: 13386–13387
Koike et al. *J. Am. Chem. Soc.* 1996, 118, 12696–12703.
Kovacs, Z.; Sherry, A. D. *Tet. Lett.* 1995, 51, 9269–9272.
Lakowicz, J. R. *Principles of Fluorescence Spectroscopy;* 2nd ed.; Kluwe Academic/Plenum: New York, 1999.
Lippard et al. Principles of Bioinorganic Chemistry; 1st ed.; University Science Books: Mill Valley, 1994.
Mahadevan et al. *Aust. J. Chem.* 1996, 49, 561–568.
McBryde, W. A. E. *Talanta* 1974, 21: 979–1004
Nasir et al. *JBIC* 1999, 4, 775–783.
Nasir, et al. *JBIC* 1999, 4: 775–783
Palmiter et al. *EMBO J.* 1995, 14: 639–649
Palmiter, et al. *EMBO J.* 1996, 15: 1784–1791
Palmiter, et al. *Proc. Natl. Acad. Sci. USA* 1992, 89: 6333–6337
Palmiter, et al. *Proc. Natl. Acad. Sci. USA* 1996, 93: 14934–14939
Pountney, et al. *FEBS Lett.* 1994, 345: 193–197
Prasad et al. *J. Chem. Soc. Perkin Trans.* 1991, 3329–3332.
Romary et al. *J. Chem. Soc (C)* 1968, 2884–2887.
Sato et al. *Synthesis* 1992, 539–540.
Sen, et al. *J. Indian Chem. Soc.* 1929, 6, 505.
Sen, et al. *J. Indian Chem. Soc.* 1929, 6, 51.
Shaughnessy et al. *J. Am. Chem. Soc.* 1999, 121, 2123–2132.
Slomianka, L. *Neuroscience* 1992: 48, 325–352
SMART; 5.05 ed.; Bruker AXS, Inc.: Madison, Wis., 1998.
Smith, et al. *J. Chem. Soc. Perkin Trans.* 1993, 1195–1204.
Sun et al. *J. Org. Chem.* 1997, 62, 6469–6475.
Tsien, R. Y. *Ann. Rev. Neurosci.* 1989, 12, 227–253.
Tsien, R. Y. *Fluorescent and Photochemical Probes of Dynamic Biochemical Signals Inside Living Cells;* Czarnik, A. W., Ed.; American Chemical Society: Washington D.C., 1993; Vol. 538, pp 130–146.
Tsuji, et al. *EMBO J.* 1992, 11: 4843–4850
Uchida, et al. *Neuron* 1991, 7: 337–347
Vallee et al. *Physiol. Rev.* 1993, 73: 79–118
Walkup et al. *J. Am. Chem Soc.* 2000, 122: 5644–5645
Walkup et al. *J. Am. Chem Soc.* 2000: 122: S1-S7
Wolf, H. U. *Experientia* 1973, 29: 241–249
Wolfe et al. *J. Org. Chem.* 2000, 65, 1144–1157.
Wolfeet al. *J. Org. Chem.* 2000, 65, 1158–1174.
Zalewski et al. *Biochem. J.* 1993, 296, 403–408.
Zhang et al. *J. Org. Chem.* 2000, 65, 8027–8031.
U.S. Pat. No. 6,013,802
U.S. Pat. No. 6,083,758

U.S. Pat. No. 6,063,637
U.S. Pat. No. 5,986,094
U.S. Pat. No. 5,756,771
U.S. Pat. No. 4,510,251

Equivalents

The invention now being fully described, it will be apparent to one of ordinary skill in the art that many changes and modifications may be made thereto without requiring more than routine experimentation or departing from the spirit or scope of the appended claims.

What is claimed is:

1. A ligand for metal ions, comprising the following moiety:

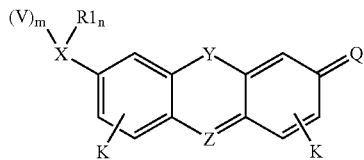

wherein:
X is N;
Q is O, S or Se;
K is selected independently and optionally from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN;
V is independently each a Lewis base capable of forming one or more coordination bonds with a metal ion, and in the case when m is 2, both V do not contain —$CO_2H$ disposed in a manner to allow for coordination of both of said —$CO_2H$ to a single metal ion;
R1 is independently hydrogen, alkyl, cycloalkyl, aryl, aryl, heterocycle or heterocycle;
m is 1 or 2, and n is equal to (2−m);
Y is O, S, Se, NR1, or $C(CH_3)_3$; and
Z is N, $HOOCCH_2CH_2C$, HOOC—CH=CH—C, (2-carboxyphenyl)-C, (2-sulfophenyl)-C, (2-carboxy-3,4,5,6-tetrachlorophenyl)-C, (2-carboxy-4-nitrophenyl)-C, (2-carboxy-5-nitrophenyl)-C, (2-carboxy-4-aminophenyl)-C, (2-carboxy-5-aminoyphenyl)-C, (2,4-dicarboxyphenyl)-C, (2,5-dicarboxylphenyl)-C, (2,4,5-tricarboxyphenyl)C-, and other substituted (2-carboxyphenyl)-C moieties.

2. The ligand for metal ions of claim 1, wherein Q is OA, wherein A is hydrogen, alkyl, cycloalkyl, aryl, aryl, heterocycle, heterocycle or a hydroxyl protecting-group and Z forms a tautomer different from the tautomer formed when Q is O.

3. The ligand for metal ions of claim 1, wherein m is 2 and the two V's form a ring structure with X.

4. The ligand for metal ions of claim 3, wherein said ligand for metal ion is sterically capable of forming four or more coordinate bonds to a single metal ion.

5. The ligand for metal ions of claim 1, wherein m is 2 and each of the V's are capable of coordinating to a single metal ion through at least one nitrogen atom.

6. The ligand for metal ions of claim 1, wherein m is 2 and at least one of the V's is capable of coordinating to a single metal ion through only one nitrogen atom.

7. A coordination complex, comprising a metal ion coordinated to a ligand for metal ions of claim 1.

8. A coordination complex, comprising a metal ion coordinated to a ligand for metal ions of claim 3.

9. The coordination complex of claim 7, wherein said metal ion is $Zn^{2+}$.

10. The coordination complex of claim 8, wherein said metal ion is $Zn^{2+}$.

11. A method of detecting, and optionally quantifying the concentration of, a metal ion in a sample, comprising:
   a. Measuring the fluorescence of a ligand for metal ions of claim 1 or 2 in the uncoordinated form;
   b. Measuring the fluorescence of a sample;
   c. Adding to said sample said ligand for metal ions;
   d. Measuring the fluorescence of said ligand in said sample;
   e. Comparing the fluorescence measurements from steps (a), (b) and (d); and
   f. Providing instructions on how to determine whether a metal ion is present in said sample, and optionally instructions on how to determine the concentration of said metal ion in said sample, by comparing said fluorescence measurements, wherein an increase in the fluorescence of said ligand upon addition to said sample indicates the presence of a metal ion.

12. A method of detecting, and optionally quantifying the concentration of, a metal ion in a sample, comprising:
   a. Measuring the fluorescence of a ligand for metal ions of claim 1 or 2 in the uncoordinated form;
   b. Adding to a sample said ligand for metal ions;
   c. Measuring the fluorescence of said ligand in said sample;
   d. Comparing the fluorescence measurements from steps (a) and (c); and
   e. Determining whether a metal ion is present in said sample as indicated by an increase in fluorescence between steps (a) and (c), and optionally said concentration of said metal ion by reference to standards.

13. The method of claim 11, wherein said sample is a cell.

14. The method of claim 12, wherein said sample is a cell.

15. The method of claim 11, wherein said sample is in vitro.

16. The method of claim 12, wherein said sample is in vitro.

17. The method of claim 11, further comprising measuring the fluorescence of said ligand in the uncoordinated form at a different concentration of said ligand from said first measurement.

18. The method of claim 12, further comprising measuring the fluorescence of said ligand in said sample at a different concentration of said ligand.

19. The method of claim 11, wherein said metal ion is $Zn^{2+}$.

20. The method of claim 12, wherein said metal ion is $Zn^{2+}$.

21. The method of claim 11, wherein said sample contains a metal ion that is toxic to mammals.

22. The method of claim 12, wherein said sample contains a metal ion that is toxic to mammals.

* * * * *

UNITED STATES PATENT AND TRADEMARK OFFICE
CERTIFICATE OF CORRECTION

PATENT NO. : 7,018,840 B2  Page 1 of 1
APPLICATION NO. : 10/124742
DATED : March 28, 2006
INVENTOR(S) : Stephen J. Lippard et al.

It is certified that error appears in the above-identified patent and that said Letters Patent is hereby corrected as shown below:

Column 1, lines 14-19, replace:

"This invention was made in part with support from the U.S. Government under a grant awarded by the National Cancer Institute, National Cancer Institute National Research Service Award, and Grant Number 1-R01-GM65519-01 awarded by the NIH. Accordingly, the U.S. Government has certain rights in this invention."

with

--This invention was made with government support under Grant No. R01 GM065519, awarded by the National Institutes of Health. The government has certain rights in this invention.--

Signed and Sealed this
Fourteenth Day of June, 2011

David J. Kappos
*Director of the United States Patent and Trademark Office*